US011253685B2

United States Patent
Fahey et al.

(10) Patent No.: US 11,253,685 B2
(45) Date of Patent: Feb. 22, 2022

(54) IMPLANTABLE SHUNT SYSTEMS AND METHODS

(71) Applicant: Shifamed Holdings, LLC, Campbell, CA (US)

(72) Inventors: Brian Fahey, Menlo Park, CA (US); Peter Andriola, Castro Valley, CA (US); William Jason Fox, San Mateo, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/298,396

(22) PCT Filed: Dec. 4, 2020

(86) PCT No.: PCT/US2020/063360
§ 371 (c)(1),
(2) Date: May 28, 2021

(87) PCT Pub. No.: WO2021/113670
PCT Pub. Date: Jun. 10, 2021

(65) Prior Publication Data
US 2021/0370032 A1 Dec. 2, 2021

Related U.S. Application Data

(60) Provisional application No. 62/952,903, filed on Dec. 23, 2019, provisional application No. 62/952,894, (Continued)

(51) Int. Cl.
*A61M 27/00* (2006.01)
*A61M 60/892* (2021.01)
(Continued)

(52) U.S. Cl.
CPC ........ *A61M 27/002* (2013.01); *A61M 60/165* (2021.01); *A61M 60/30* (2021.01);
(Continued)

(58) Field of Classification Search
CPC .. A61M 27/002; A61M 60/892; A61M 60/30; A61M 60/876; A61M 60/165;
(Continued)

(56) References Cited

U.S. PATENT DOCUMENTS 6,077,298 A 6/2000 Tu et al.
6,120,534 A 9/2000 Ruiz
(Continued)

FOREIGN PATENT DOCUMENTS

AU 2005211243 8/2005
AU 2010344182 8/2012
(Continued)

OTHER PUBLICATIONS

Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.
(Continued)

*Primary Examiner* — Ariana Zimbouski
(74) *Attorney, Agent, or Firm* — Perkins Coie LLP

(57) ABSTRACT

The present technology relates to interatrial shunting systems and methods. In some embodiments, the present technology includes interatrial shunting systems that include a shunting element having a lumen extending therethrough that is configured to fluidly couple the left atrium and the right atrium when the shunting element is implanted in a patient. The system can also include an energy receiving component for receiving energy from an energy source positioned external to the body, an energy storage compo-
(Continued)

nent for storing the received energy, and/or a flow control mechanism for adjusting a geometry of the lumen.

44 Claims, 9 Drawing Sheets

Related U.S. Application Data filed on Dec. 23, 2019, provisional application No. 62/944,193, filed on Dec. 5, 2019.

(51) Int. Cl.
*A61M 60/165* (2021.01)
*A61M 60/30* (2021.01)
*A61M 60/876* (2021.01)

(52) U.S. Cl.
CPC ........ *A61M 60/876* (2021.01); *A61M 60/892* (2021.01); *A61M 2205/0266* (2013.01); *A61M 2205/3368* (2013.01); *A61M 2210/125* (2013.01)

(58) Field of Classification Search
CPC .... A61M 2210/125; A61M 2205/0266; A61M 2205/3368; A61F 2/2418; A61F 2/24
See application file for complete search history.

(56) References Cited

U.S. PATENT DOCUMENTS

| | | | |
|---|---|---|---|
| 6,165,209 A | 12/2000 | Patterson et al. | |
| 6,240,322 B1 | 5/2001 | Peterfeso et al. | |
| 6,783,499 B2 | 8/2004 | Schwartz | |
| 6,909,920 B2 | 6/2005 | Lokhoff et al. | |
| 7,524,329 B2 | 4/2009 | Rucker | |
| 7,617,001 B2 | 11/2009 | Penner et al. | |
| 7,634,318 B2 | 12/2009 | Tran et al. | |
| 7,860,579 B2 | 12/2010 | Goetzinger et al. | |
| 8,043,360 B2 | 10/2011 | McNamara et al. | |
| 8,070,708 B2 | 12/2011 | Rettenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,235,933 B2 | 8/2012 | Keren et al. | |
| 8,252,042 B2 | 8/2012 | McNamara et al. | |
| 8,328,751 B2 | 12/2012 | Keren et al. | |
| 8,460,372 B2 | 6/2013 | McNamara et al. | |
| 8,696,611 B2 | 4/2014 | Nitzan et al. | |
| 8,740,962 B2 | 6/2014 | Finch et al. | |
| 8,745,845 B2 | 6/2014 | Finch et al. | |
| 8,752,258 B2 | 6/2014 | Finch et al. | |
| 8,882,697 B2 | 11/2014 | Celermajer et al. | |
| 8,951,223 B2 | 2/2015 | McNamara et al. | |
| 9,005,155 B2 | 4/2015 | Sugimoto | |
| 9,034,034 B2 | 5/2015 | Nitzan et al. | |
| 9,204,842 B2 | 12/2015 | Mothilal et al. | |
| 9,205,236 B2 | 12/2015 | McNamara et al. | |
| 9,232,997 B2 | 1/2016 | Sugimoto et al. | |
| 9,277,995 B2 | 3/2016 | Celermajer et al. | |
| 9,358,371 B2 | 6/2016 | McNamara et al. | |
| 9,456,812 B2 | 10/2016 | Finch et al. | |
| 9,610,041 B2 | 4/2017 | Foster et al. | |
| 9,629,715 B2 | 4/2017 | Nitzan et al. | |
| 9,642,993 B2 | 5/2017 | McNamara et al. | |
| 9,649,480 B2 | 5/2017 | Sugimoto et al. | |
| 9,681,948 B2 * | 6/2017 | Levi | A61F 2/2409 |
| 9,707,382 B2 | 7/2017 | Nitzan et al. | |
| 9,713,696 B2 | 7/2017 | Yacoby et al. | |
| 9,724,499 B2 | 8/2017 | Rettenberg et al. | |
| 9,757,107 B2 | 9/2017 | McNamara et al. | |
| 9,775,636 B2 | 10/2017 | Fazio et al. | |
| 9,918,856 B2 | 3/2018 | Favier et al. | |
| 9,937,036 B2 | 4/2018 | Sugimoto et al. | |
| 9,943,670 B2 | 4/2018 | Keren et al. | |
| 9,980,815 B2 | 5/2018 | Nitzan et al. | |
| 10,045,766 B2 | 8/2018 | McNamara et al. | |
| 10,076,403 B1 | 9/2018 | Eigler et al. | |
| 10,188,375 B2 | 1/2019 | McNamara et al. | |
| 10,207,087 B2 | 2/2019 | Keren | |
| 10,251,740 B2 | 4/2019 | Eigler et al. | |
| 10,292,690 B2 | 5/2019 | Celermajer et al. | |
| 10,357,357 B2 | 7/2019 | Levi et al. | |
| 10,368,981 B2 | 8/2019 | Nitzan et al. | |
| 10,376,680 B2 | 8/2019 | McNamara et al. | |
| 10,398,421 B2 | 9/2019 | Celermajer | |
| 10,405,903 B1 | 9/2019 | Biesinger et al. | |
| 10,413,284 B2 | 9/2019 | McNamara et al. | |
| 10,413,286 B2 | 9/2019 | McNamara et al. | |
| 10,463,477 B2 | 11/2019 | Forcucci et al. | |
| 10,463,490 B2 | 11/2019 | Rettenberg et al. | |
| 10,471,251 B1 | 11/2019 | Manicka | |
| 10,478,594 B2 | 11/2019 | Yacoby et al. | |
| 10,568,751 B2 | 2/2020 | McNamara | |
| 10,588,611 B2 | 3/2020 | Magnin et al. | |
| 10,610,210 B2 | 4/2020 | Finch et al. | |
| 10,624,621 B2 | 4/2020 | Celermajer | |
| 10,632,292 B2 | 4/2020 | Forcucci et al. | |
| 10,639,459 B2 | 5/2020 | Nitzan et al. | |
| 10,675,450 B2 | 6/2020 | Finch | |
| 10,828,151 B2 | 11/2020 | Nitzan et al. | |
| 10,835,394 B2 | 11/2020 | Nae et al. | |
| 10,898,698 B1 | 1/2021 | Eigler et al. | |
| 10,912,645 B2 | 2/2021 | Rettenberg et al. | |
| 10,925,706 B2 | 2/2021 | Eigler et al. | |
| 10,932,786 B2 | 3/2021 | McNamara et al. | |
| 10,940,296 B2 | 3/2021 | Keren | |
| 2002/0072656 A1 | 6/2002 | Vantassel et al. | |
| 2002/0177891 A1 | 11/2002 | Miles et al. | |
| 2003/0127090 A1 | 7/2003 | Gifford et al. | |
| 2004/0158143 A1 | 8/2004 | Flaherty et al. | |
| 2004/0186566 A1 | 9/2004 | Hindrichs et al. | |
| 2005/0148925 A1 * | 7/2005 | Rottenberg | A61B 5/0215 604/9 |
| 2005/0204811 A1 | 9/2005 | Neff | |
| 2005/0288722 A1 | 12/2005 | Eigler et al. | |
| 2006/0009810 A1 | 1/2006 | Mann et al. | |
| 2006/0047205 A1 | 3/2006 | Ludomirsky et al. | |
| 2006/0200030 A1 | 9/2006 | White et al. | |
| 2007/0010837 A1 | 1/2007 | Tanaka | |
| 2007/0088220 A1 | 4/2007 | Stahmann | |
| 2007/0150019 A1 | 6/2007 | Youker et al. | |
| 2007/0282157 A1 | 12/2007 | Rottenberg et al. | |
| 2008/0033527 A1 | 2/2008 | Nunez et al. | |
| 2008/0097276 A1 | 4/2008 | Bertrand et al. | |
| 2008/0108904 A1 | 5/2008 | Heil | |
| 2008/0119891 A1 | 5/2008 | Miles et al. | |
| 2008/0171941 A1 | 7/2008 | Huelskamp et al. | |
| 2008/0208083 A1 | 8/2008 | Lin et al. | |
| 2009/0036975 A1 | 2/2009 | Ward et al. | |
| 2009/0243956 A1 | 10/2009 | Keilman et al. | |
| 2009/0270742 A1 | 10/2009 | Wolinsky et al. | |
| 2009/0281597 A1 | 11/2009 | Parramon et al. | |
| 2010/0063375 A1 | 3/2010 | Kassab et al. | |
| 2010/0076366 A1 | 3/2010 | Henderson, Sr. et al. | |
| 2010/0076517 A1 | 3/2010 | Imran | |
| 2010/0106028 A1 | 4/2010 | Penner et al. | |
| 2010/0168672 A1 | 7/2010 | Carr | |
| 2010/0179449 A1 | 7/2010 | Chow et al. | |
| 2010/0249560 A1 | 9/2010 | Levinson et al. | |
| 2010/0262021 A1 | 10/2010 | Yadav et al. | |
| 2010/0262036 A1 | 10/2010 | Najafi et al. | |
| 2010/0298930 A1 | 11/2010 | Orlov | |
| 2011/0082377 A1 | 4/2011 | Mahajan et al. | |
| 2011/0218480 A1 | 9/2011 | Rettenberg et al. | |
| 2011/0218481 A1 | 9/2011 | Rettenberg et al. | |
| 2011/0257723 A1 | 10/2011 | McNamara | |
| 2011/0264194 A1 | 10/2011 | Griswold | |
| 2011/0295183 A1 | 12/2011 | Finch et al. | |
| 2012/0265296 A1 | 10/2012 | McNamara et al. | |
| 2012/0290062 A1 | 11/2012 | McNamara et al. | |
| 2013/0123569 A1 | 5/2013 | Gross | |
| 2013/0144379 A1 | 6/2013 | Najafi et al. | |
| 2013/0178783 A1 | 7/2013 | McNamara et al. | |

(56) References Cited

U.S. PATENT DOCUMENTS

| | | |
|---|---|---|
| 2013/0178784 A1 | 7/2013 | McNamara et al. |
| 2013/0192611 A1 | 8/2013 | Taepke, II et al. |
| 2013/0197423 A1 | 8/2013 | Keren et al. |
| 2013/0253343 A1 | 9/2013 | Waldhauser et al. |
| 2014/0012342 A1 | 1/2014 | Penner et al. |
| 2014/0046427 A1 | 2/2014 | Michalak |
| 2014/0128795 A1 | 5/2014 | Keren et al. |
| 2014/0128796 A1 | 5/2014 | Keren et al. |
| 2014/0135647 A1 | 5/2014 | Wolf, II |
| 2014/0163449 A1 | 6/2014 | Rottenberg et al. |
| 2014/0213959 A1 | 7/2014 | Nitzan et al. |
| 2014/0222040 A1 | 8/2014 | Park et al. |
| 2014/0277054 A1 | 9/2014 | McNamara et al. |
| 2014/0306807 A1 | 10/2014 | Rowland et al. |
| 2015/0034217 A1 | 2/2015 | Vad |
| 2015/0119796 A1 | 4/2015 | Finch |
| 2015/0148731 A1 | 5/2015 | McNamara et al. |
| 2015/0157268 A1 | 6/2015 | Winshtein et al. |
| 2015/0208929 A1 | 7/2015 | Rowland et al. |
| 2015/0223707 A1 | 8/2015 | Ludoph |
| 2015/0230843 A1 | 8/2015 | Palmer et al. |
| 2016/0151179 A1 | 6/2016 | Favier et al. |
| 2016/0158561 A1 | 6/2016 | Reddy |
| 2016/0235999 A1 | 8/2016 | Nuta et al. |
| 2017/0014067 A1 | 1/2017 | Peppou et al. |
| 2017/0105635 A1 | 4/2017 | Cho et al. |
| 2017/0113026 A1 | 4/2017 | Finch |
| 2017/0312078 A1 | 11/2017 | Krivoruchko |
| 2017/0340460 A1 | 11/2017 | Rosen et al. |
| 2018/0014828 A1 | 1/2018 | Fonte et al. |
| 2018/0168463 A1 | 6/2018 | Morris et al. |
| 2018/0256865 A1 | 9/2018 | Finch et al. |
| 2018/0262037 A1 | 9/2018 | Meskens |
| 2019/0000327 A1 | 1/2019 | Doan et al. |
| 2019/0015103 A1 | 1/2019 | Sharma |
| 2019/0021861 A1 | 1/2019 | Finch |
| 2019/0167197 A1 | 6/2019 | Abuuassar et al. |
| 2019/0173505 A1 | 6/2019 | Koyama |
| 2019/0192864 A1 | 6/2019 | Koop et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0328513 A1 | 10/2019 | Levi et al. |
| 2019/0336163 A1 | 11/2019 | McNamara et al. |
| 2020/0060825 A1 | 2/2020 | Rettenberg et al. |
| 2020/0078196 A1 | 3/2020 | Rosen et al. |
| 2020/0078558 A1 | 3/2020 | Yacoby et al. |
| 2020/0188143 A1 | 6/2020 | McNamara |
| 2020/0229977 A1 | 7/2020 | Mixter et al. |
| 2020/0229982 A1 | 7/2020 | Mixter et al. |
| 2020/0245991 A1 | 8/2020 | Celermajer |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0052378 A1 | 2/2021 | Nitzan et al. |
| 2021/0085935 A1 | 3/2021 | Fahey et al. |
| 2021/0100665 A1 | 4/2021 | Nae et al. |
| 2021/0121179 A1 | 4/2021 | Ben-David et al. |
| 2021/0205590 A1 | 7/2021 | Fahey et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 105662653 | 6/2013 |
| CN | 103458832 | 12/2013 |
| CN | 109646063 A | 4/2019 |
| CN | 110536657 | 12/2019 |
| EP | 1112044 | 1/2007 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3329860 | 6/2018 |
| EP | 3589238 | 1/2020 |
| EP | 3740163 | 11/2020 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2020509812 | 4/2020 |
| WO | WO2005074367 | 8/2005 |
| WO | WO2006089236 | 8/2006 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2017151566 | 9/2017 |
| WO | WO2018024868 | 2/2018 |
| WO | WO2018132549 | 7/2018 |
| WO | WO2018158747 | 9/2018 |
| WO | WO2019142152 | 1/2019 |
| WO | WO2019186101 | 2/2019 |
| WO | WO2019142152 | 7/2019 |
| WO | WO2019175401 | 9/2019 |
| WO | WO2020123338 | 6/2020 |
| WO | WO2020132678 | 6/2020 |
| WO | WO20200110048 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020217194 | 10/2020 |
| WO | WO2020225757 | 11/2020 |
| WO | WO2020234751 | 11/2020 |
| WO | WO2021050589 | 3/2021 |
| WO | WO2021072315 | 4/2021 |
| WO | WO2021126699 | 6/2021 |
| WO | WO2021150765 | 7/2021 |
| WO | WO2021159001 | 8/2021 |
| WO | WO202117059 | 10/2021 |

(56) References Cited

FOREIGN PATENT DOCUMENTS

| WO | WO2021212011 | 10/2021 |
|---|---|---|
| WO | WO2021216964 | 10/2021 |
| WO | WO2021217055 | 10/2021 |

OTHER PUBLICATIONS

Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.

International Search Report and Written Opinion received for International Application No. PCT/US19/69106 filed Dec. 31, 2019; Applicant: Shifamed Holdings, LLC; dated Mar. 23, 2020; 10 pages.

International Search Report and Written Opinion received for International Application No. PCT/US20/49996 filed Sep. 9, 2020; Applicant: Shifamed Holdings, LLC; dated Feb. 17, 2021; 16 pages.

International Search Report and Written Opinion received for International Application No. PCT/US20/64529 filed Dec. 11, 2020; Applicant: Shifamed Holdings, LLC; dated Apr. 8, 2021; 12 pages.

International Search Report and Written Opinion received for International Application No. PCT/US19/68354, filed Dec. 23, 2019; Applicant: Shifamed Holdings, LLC; dated Mar. 17, 2020; 11 pages.

International Search Report and Written Opinion received for International Application No. PCT/US21/16932, filed Feb. 5, 2021; Applicant: Shifamed Holdings, LLC; dated Jun. 3, 2021; 11 pages.

International Search Report and Written Opinion received for International Application No. PCT/US21/14433, filed Jan. 21, 2021; Applicant: Shifamed Holdings, LLC; dated May 14, 2021; 16 pages.

International Search Report and Written Opinion received for International Application No. PCT/US21/14428, filed Jan. 21, 2021; Applicant: Shifamed Holdings, LLC; dated Jun. 8, 2021; 17 pages.

International Search Report and Written Opinion received for International Application No. PCT/US2020/063360 filed Dec. 4, 2020; Applicant: Shifamed Holdings, LLC; dated Apr. 5, 2021, 13 pages.

International Search Report and Written Opinion received for International Application No. PCT/US21/28931, filed Apr. 23, 2021; Applicant: Shifamed Holdings, LLC; dated Sep. 24, 2021; 20 pages.

International Search Report and Written Opinion received for International Application No. PCT/US21/27747, filed Apr. 16, 2021; Applicant: Shifamed Holdings, LLC; dated Oct. 1, 2021; 16 pages.

International Search Report and Written Opinion received for International Application No. PCT/US20/12059, filed Jan. 2, 2020; Applicant: Shifamed Holdings, LLC; dated Jun. 5, 2020; 12 pages.

International Search Report and Written Opinion received for International Application No. PCT/US20/25509, filed Mar. 27, 2020; Applicant: Shifamed Holdings, LLC; dated Jun. 25, 2020; 9 pages.

International Search Report and Written Opinion received for International Application No. PCT/US20/26738, filed Apr. 3, 2020; Applicant: Shifamed Holdings, LLC; dated Jun. 30, 2020; 8 pages.

* cited by examiner

IMPLANTABLE SHUNT SYSTEMS AND METHODS

CROSS-REFERENCE TO RELATED APPLICATION(S)

This application is a 35 U.S.C. § 371 U.S. National Phase application of International Patent Application No. PCT/US2020/063360, filed Dec. 4, 2020, and entitled IMPLANTABLE SHUNT SYSTEMS AND METHODS, WHICH CLAIMS THE BENEFIT OF THE FOLLOWING PROVISIONAL APPLICATIONS:

(a) U.S. Provisional Patent App. No. 62/944,193, filed Dec. 5, 2019;
(b) U.S. Provisional Patent App. No. 62/952,894, filed Dec. 23, 2019; and
(c) U.S. Provisional Patent App. No. 62/952,903, filed Dec. 23, 2019.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology generally relates to implantable medical devices and, in particular, to implantable interatrial systems and associated methods for selectively controlling blood flow between the right atrium and the left atrium of a heart.

BACKGROUND

Heart failure is a medical condition associated with the inability of the heart to effectively pump blood to the body. Heart failure affects millions of people worldwide, and may arise from multiple root causes, but is generally associated with myocardial stiffening, myocardial shape remodeling, and/or abnormal cardiovascular dynamics. Chronic heart failure is a progressive disease that worsens considerably over time. Initially, the body's autonomic nervous system adapts to heart failure by altering the sympathetic and parasympathetic balance. While these adaptations are helpful in the short-term, over a longer period of time they may serve to make the disease worse.

Heart failure (HF) is a medical term that includes both heart failure with reduced ejection fraction (HFrEF) and heart failure with preserved ejection fraction (HFpEF). The prognosis with both HFpEF and HFrEF is poor; one-year mortality is 26% and 22%, respectively, according to one epidemiology study. In spite of the high prevalence of HFpEF, there remain limited options for HFpEF patients. Pharmacological therapies have been shown to impact mortality in HFrEF patients, but there are no similarly-effective evidence-based pharmacotherapies for treating HFpEF patients. Current practice is to manage and support patients while their health continues to decline.

A common symptom among heart failure patients is elevated left atrial pressure. In the past, clinicians have treated patients with elevated left atrial pressure by creating a shunt between the left and right atria using a blade or balloon septostomy. The shunt decompresses the left atrium (LA) by relieving pressure to the right atrium (RA) and systemic veins. Over time, however, the shunt typically will close or reduce in size. More recently, percutaneous interatrial shunt devices have been developed which have been shown to effectively reduce left atrial pressure. However, these percutaneous devices often have an annular passage with a fixed diameter which fails to account for a patient's changing physiology and condition. For this reason, existing percutaneous shunt devices may have a diminishing clinical effect after a period of time. Many existing percutaneous shunt devices typically are also only available in a single size that may work well for one patient but not another. Also, sometimes the amount of shunting created during the initial procedure is later determined to be less than optimal months later. Accordingly, there is a need for improved devices, systems, and methods for treating heart failure patients, particularly those with elevated left atrial pressure.

DETAILED DESCRIPTION

Figure 1:
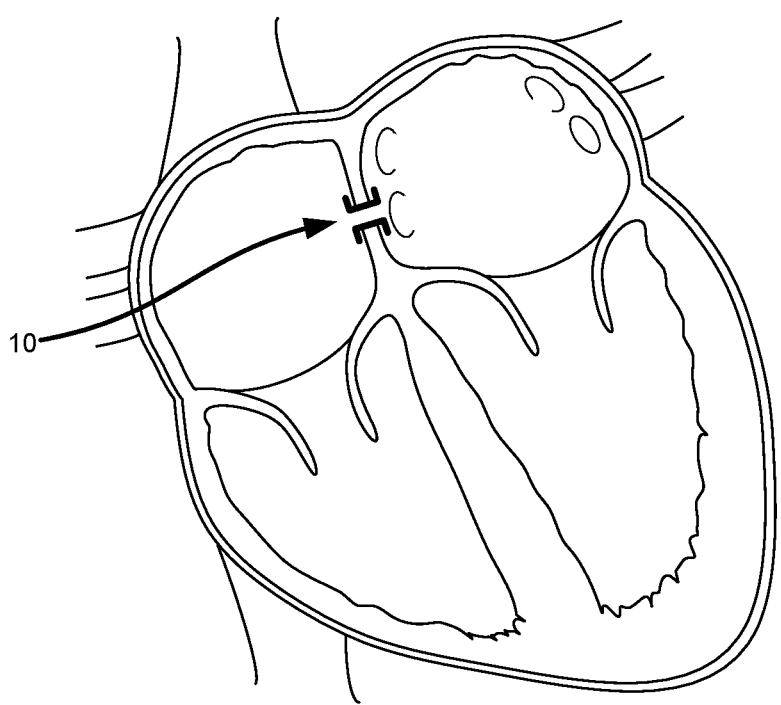
FIG. 1 is a schematic illustration of an interatrial device implanted in a heart and configured in accordance with select embodiments of the present technology.

The present technology is generally directed to implantable shunt systems and associated methods. The implantable shunt systems described herein can be used to shunt bodily fluid such as blood between a first body region and a second body region. The implantable shunt systems can include, among other things, a shunting element defining a lumen for fluidly connecting the first body region and the second body region, an actuation mechanism for adjusting a geometry of the lumen, an energy receiving component, an energy storage component, and/or one or more sensors.

For example, in some embodiments the present technology provides an interatrial shunt system. The system includes a shunting element implantable into a patient at or adjacent to a septal wall. The shunting element can fluidly connect a LA and a RA of the patient to facilitate blood flow therebetween. For example, the shunting element can have a lumen extending therethrough between a first orifice positionable in the LA and a second orifice positionable in the RA. The system can further include (i) an actuation mechanism configured to selectively adjust a geometry of the lumen, the first orifice, and/or the second orifice, (ii) an implantable energy receiving component configured to receive energy from an energy source positioned external to the patient, and (iii) an implantable energy storage component configured to store energy received by the implantable energy receiving component. The implantable energy storage component can selectively release the stored energy to power the actuation mechanism and/or one or more active components of the system, such as one or more sensors.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-8C.

Reference throughout this specification to "one embodiment" or "an embodiment" means that a particular feature, structure or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "substantially," "approximately," and "about" are used herein to mean the stated value plus or minus 10%.

As used herein, in various embodiments, the terms "interatrial device," "interatrial shunt device," "IAD," "IASD," "interatrial shunt," and "shunt" are used interchangeably and, in at least one configuration, refer to a shunting element that provides a blood flow between a first region (e.g., a LA of a heart) and a second region (e.g., a RA or coronary sinus of the heart) of a patient. Although described in terms of a shunt between the atria, namely the LA and the RA, one will appreciate that the technology may be applied equally to other medical devices. For example, the shunt may be positioned between other chambers and passages of the heart or other parts of the cardiovascular system. For example, any of the shunts described herein, including those referred to as "interatrial," may be nevertheless used and/or modified to shunt between the LA and the coronary sinus, or between the right pulmonary vein and the superior vena cava. Moreover, while the disclosure herein primarily describes shunting blood from the LA to the RA, the present technology can be readily adapted to shunt blood from the RA to the LA to treat certain conditions, such as pulmonary hypertension. For example, mirror images of embodiments, or in some cases identical embodiments, used to shunt blood from the LA to the RA can be used to shunt blood from the RA to the LA in certain patients. In another example, the shunt may be used to facilitate flow between an organ and organ, organ and vessel, etc. The shunt may also be used for fluids other than blood. The technologies described herein may be used for an ophthalmology shunt to flow aqueous or fluids to treat gastrointestinal disorders. The technologies described herein may also be used for controlled delivery of other fluids such as saline, drugs, or pharmacological agents.

As used herein, the terms "interatrial shunt system," "interatrial shunting systems," "shunting systems," and the like are used interchangeably to refer to an implantable system that, among other things, includes an interatrial shunt (e.g., a shunting element).

As used herein, the term "geometry" can include the size and/or the shape of an element. Accordingly, when the present disclosure describes a change in geometry, it can refer to a change in the size of an element (e.g., moving from a smaller circle to a larger circle), a change in the shape of an element (e.g., moving from a circle to an oval), and/or a change in the shape and size of an element (e.g., moving from a smaller circle to a larger oval). In various embodiments, "geometry" refers to the relative arrangements and/or positions of elements in the respective system.

The headings provided herein are for convenience only and do not interpret the scope or meaning of the claimed present technology.

A. Interatrial Shunts for Treatment of Heart Failure

Heart failure can be classified into one of at least two categories based upon the ejection fraction a patient experiences: (1) HFpEF, historically referred to as diastolic heart failure or (2) HFrEF, historically referred to as systolic heart failure. One definition of HFrEF is a left ventricular ejection fraction lower than 35%-40%. Though related, the underlying pathophysiology and the treatment regimens for each heart failure classification may vary considerably. For example, while there are established pharmaceutical therapies that can help treat the symptoms of HFrEF, and at times slow or reverse the progression of the disease, there are limited available pharmaceutical therapies for HFpEF with only questionable efficacy.

In heart failure patients, abnormal function in the left ventricle (LV) leads to pressure build-up in the LA. This leads directly to higher pressures in the pulmonary venous system, which feeds the LA. Elevated pulmonary venous pressures push fluid out of capillaries and into the lungs. This fluid build-up leads to pulmonary congestion and many of the symptoms of heart failure, including shortness of breath and signs of exertion with even mild physical activity. Risk factors for HF include renal dysfunction, hypertension, hyperlipidemia, diabetes, smoking, obesity, old age, and obstructive sleep apnea. HF patients can have increased stiffness of the LV which causes a decrease in left ventricular relaxation during diastole resulting in increased pressure and inadequate filling of the ventricle. HF patients may also have an increased risk for atrial fibrillation and pulmonary hypertension, and typically have other comorbidities that can complicate treatment options.

Interatrial shunts have recently been proposed as a way to reduce elevated left atrial pressure, and this emerging class of cardiovascular therapeutic interventions has been demonstrated to have significant clinical promise. FIG. 1, for example, shows the conventional placement of a shunt in the septal wall between the LA and RA. Most conventional interatrial shunts (e.g., shunt 10) involve creating a hole or inserting an implant with a lumen into the atrial septal wall, thereby creating a fluid communication pathway between the LA and the RA. As such, elevated left atrial pressure may be partially relieved by unloading the LA into the RA. In early clinical trials, this approach has been shown to improve symptoms of heart failure.

One challenge with many conventional interatrial shunts is determining the most appropriate size and shape of the shunt lumen. A lumen that is too small may not adequately unload the LA and relieve symptoms; a lumen that is too large may overload the RA and right-heart more generally, creating new problems for the patient. Moreover, the relationship between pressure reduction and clinical outcomes and the degree of pressure reduction required for optimized outcomes is still not fully understood, in part because the pathophysiology for HFpEF (and to a lesser extent, HFrEF) is not completely understood. As such, clinicians are forced to take a best guess at selecting the appropriately sized shunt (based on limited clinical evidence) and generally cannot adjust the sizing over time. Worse, clinicians must select the size of the shunt based on general factors (e.g., the size of the patient's anatomical structures, the patient's hemodynamic measurements taken at one snapshot in time, etc.) and/or the design of available devices rather than the individual patient's health and anticipated response. With traditional devices, the clinician does not have the ability to adjust or titrate the therapy once the device is implanted, for example, in response to changing patient conditions such as progression of disease. By contrast, interatrial shunting systems configured in accordance with embodiments of the present technology allow a clinician to select the size—perioperatively or post-implant—based on the patient.

A further challenge with conventional interatrial shunts is that function of the LA (and more generally, the cardiovascular system) can vary depending on a number of factors, for example during exercise, during periods where a patient's medication adherence has slipped, as the patient's disease progresses, or during other periods. Existing conventional shunts are generally static in nature and lack an ability to adapt to patient conditions in such a way to optimize therapy.

Other shortcomings of existing conventional interatrial shunts include: (1) shunts tending to be permanently implanted in the septal wall in a way that complicates or prevents future transseptal access, which may prohibit or complicate additional left-heart procedures that generally would require transseptal access; (2) shunts tending to be fixed and unable to adapt to changing patient conditions, such as progression of disease, and (3) a lack of sensors and/or machine-learning capability that limit the information available from the patient and limit the ability to improve therapy for the patient (or for the larger patient cohort) over time.

B. Interatrial Shunt Systems

Figure 2:
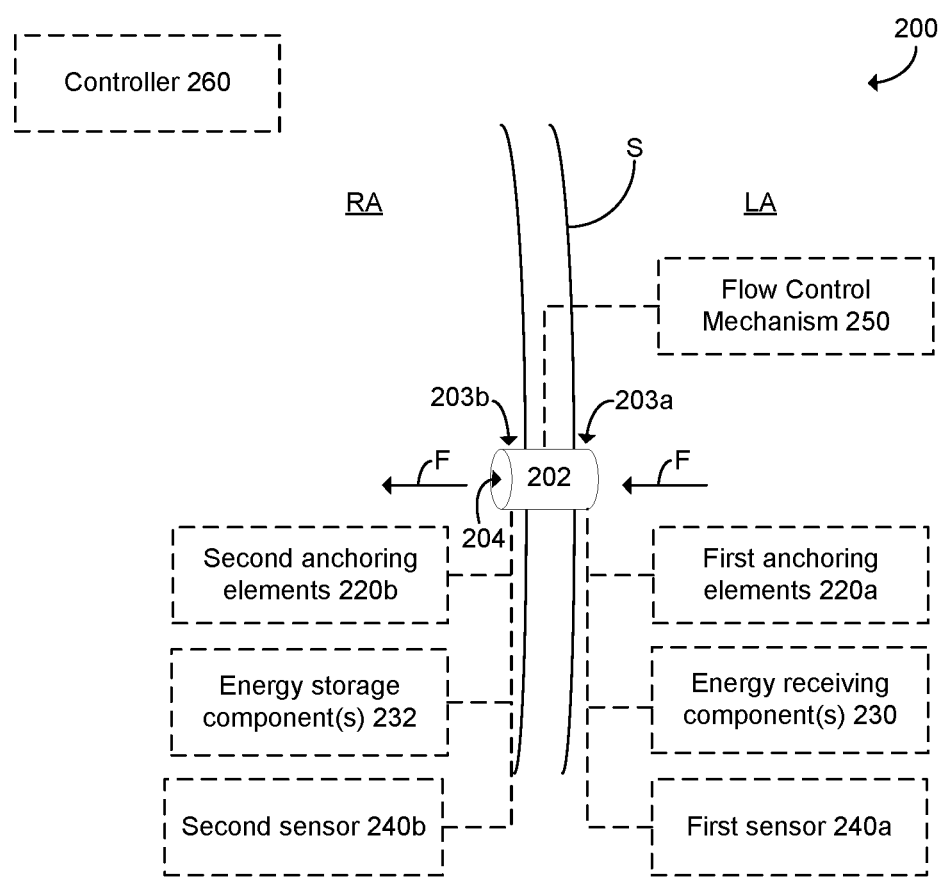
FIG. 2 is a schematic illustration of an interatrial shunting system configured in accordance with select embodiments of the present technology.

As provided above, the present technology is generally directed to implantable shunt systems, such as implantable interatrial shunt systems. FIG. 2 is a schematic illustration of an interatrial shunting system 200 ("system 200") configured in accordance with embodiments of the present technology. The system 200 includes a shunting element or device 202 defining a lumen 204 therethrough. The shunting element 202 can include a first end portion 203a positionable in the LA and a second end portion 203b positionable in the RA. Accordingly, when implanted in the septal wall S, the system 200 fluidly connects the LA and the RA via the lumen 204. When the system 200 is implanted to treat HFpEF, blood generally flows through the lumen 204 in flow direction F (i.e., from the LA to the RA). Under varying subject conditions, the lumen 204 may enable flow in the opposite direction (i.e., from the RA to the LA), or in both directions as the pressure gradient between chambers alternates.

The shunting element 202 can be stabilized in position through forces applied by aspects of the system (e.g., by a flow control mechanism 250, described below) to regions of tissue (e.g., a septal wall) and/or be secured in place by one or more anchoring element(s). For example, the system 200 can include one or more first anchoring elements 220a positioned on the LA side of the septal wall S and/or one or more second anchoring elements 220b positioned on the RA side of the septal wall S (collectively referred to as anchoring elements 220). The first anchoring elements 220a may engage a portion of the septal wall S facing the LA and the second anchoring elements 220b may engage a portion of the septal wall S facing the RA. In some embodiments, the anchoring elements 220 do not make direct contact with a tissue wall. In some embodiments, the anchoring elements 220 extend from and/or are integral with aspects of the shunting element 202. This may be a direct connection via a process such as welding, via an adhesive, or via another connection mechanism known to those skilled in the art. Alternatively, the shunting element 202 and the anchoring elements 220 may be comprised of a single structure, such as a unitary structure composed of a superelastic alloy (e.g., nitinol), and treated so each portion of the device takes on the desired shape. In various embodiments, a connecting element such as a strut or arm may be used to connect the anchoring elements 220 to a horizontal body portion of the shunting element 202. This horizontal body portion may be transseptal, partially-transseptal, or may lie predominantly on one side of the septal wall S, and may have a generally tubular shape that defines the lumen 204. In some embodiments, the system 200 includes a stent-like structure that includes the anchoring elements 220 and an outer frame portion (not shown) that directly interfaces with the septal wall S. In some embodiments, the outer frame portion may be distinct from the separate horizontal body portion that serves as a fluid communication lumen, as described in greater detail with respect to FIGS. 6-7B.

In some embodiments, the shunting element 202 is anchored in place using one or more anchoring elements positioned on only one side of the septal wall S. In yet other embodiments, the system 200 does not include first and second anchoring elements 220a and 220b and the shunting element 202 is secured in place by its general shape, by exerting a radially outward pressure, by another component of the system 200, and/or by other suitable mechanisms.

The system 200 further includes various electronic components. For example, the system 200 can include one or more energy receiving components 230 and one or more energy storage components 232. As discussed in greater detail below, the one or more energy receiving components 230 can be configured to (i) receive energy from an energy source positioned external to a patient's body, and/or (ii) generate energy when exposed to a magnetic or electric field generated by the energy source positioned external to the implanted components of the system (e.g., generated by a source external to the patient's body, generated by a catheter inside the patient's body, etc.). In some embodiments, the energy receiving component 230 can be configured to receive energy transmitted in the radiofrequency (RF) frequency range, including in the high frequency RF range (e.g., between 3-30 MHz) and/or the ultra-high frequency RF range (e.g., 300-3,000 MHz). In other embodiments, the energy receiving component 230 can be configured to receive magnetic or other forms of energy (e.g., heat). The energy receiving component 230 can be a metallic coil, wire, or other antenna, and may be composed at least in part of a high conductivity metal such as copper, silver, or composites thereof. In some embodiments, the energy receiving component 230 may be a generally circular loop or coil of multiple loops coaxial with the lumen 204. In other embodiments, the energy receiving component 230 may be an oval or other non-circular loop or coil of multiple loops bent around the lumen 204. Another embodiment may include a combination of the foregoing loop or coil of multiple loops configured to couple to an external magnetic field regardless of orientation. In some embodiments, a portion of the shunt structure (e.g., anchor elements 220) may serve as all or part of the coil or antenna.

The energy storage components 232 can be configured to store energy received and/or generated by the energy receiving component 230. The energy storage components 232 can include a battery, a supercapacitor, a capacitor, and/or other suitable elements that can retain energy. As described below, the energy received by the energy receiving component 230 and/or stored within the energy storage components 232 can be used (i) to actuate a flow control mechanism 250 to adjust a geometry of the lumen 204 (and/or a geometry of the lumen orifice), thereby altering the flow of blood through the lumen 204, (ii) to power various implanted electronic components, such as sensors 240 described below, and/or (iii) for other operations requiring an energy input.

In some embodiments, the system 200 includes more than one energy receiving component 230. For example, the system 200 can include a first energy receiving component and a second energy receiving component. The first energy receiving component and the second energy receiving component can both be in electrical communication with the energy storage component 232. The first energy receiving component can be configured to receive energy from one or more external sources configured to interface or otherwise communicate with the first energy receiving component. For example, the one or more external sources can include an energy source positioned external to the body and configured to deliver energy remotely to the energy receiving component and/or a catheter that docks or otherwise interfaces with the energy receiving component. The second energy receiving component can be configured to receive energy from the energy storage component 232. Accordingly, energy can be transferred from an external source to the first energy receiving component, from the first energy receiving component to the energy storage component, and from the energy storage component to the second energy receiving component. In some embodiments, the second energy receiving component can be part of the flow control mechanism 250, described below. In some embodiments, a component may simultaneously and/or alternatingly serve as both an energy receiving component and an energy storage component.

The first energy receiving component may be a combination of conductive (e.g. wire or PCB monopole or dipole antenna) and dielectric (e.g. dielectric rod antenna) elements capable of extracting energy from an electromagnetic field, or a conductive element (e.g. wire coil) capable of extracting energy from an AC magnetic field. In some embodiments, the first energy receiving component has substantially no temperature rise when it receives energy, but the second energy receiving component does have a temperature rise when it receives energy. In such embodiments, the first energy receiving component may receive energy from an external source and store it without meaningful dissipation (e.g. dissipation of less than 10%, 15%, or 20% of the total received energy), and later transfer it to the second energy receiving component which dissipates it intentionally. For example, the second energy receiving component may include a temperature sensitive shape memory alloy material that can transition between various configurations when heat is applied. In some embodiments, the first energy receiving component and second energy receiving component can receive energy via pulses occurring at different frequencies. For example, the first energy receiving component can receive energy delivered at a first frequency, and the second energy receiving component can receive energy delivered at a second frequency different than the first frequency. In some embodiments, the second energy receiving component receives a direct current signal. In some embodiments, the first energy receiving component receives an alternating current signal. In some embodiments, the second energy receiving component may directly receive AC energy from an external source. One or more of the electrical components (e.g., the energy receiving components or the energy storage components) can extend along an axial length of the septal implant lumen.

Accordingly, the septal implants described herein can receive energy from an external source and store the energy on the implant in an energy storage component. Upon selective activation, the energy storage component releases the energy in discrete portions. The discrete portions can be defined by the amount of energy released and/or the time period of energy release (e.g., 200 ms or less). In some embodiments, the energy may be selectively released to more than one second energy receiving component and/or to more than one location on the second energy receiving component. In some embodiments, an energy storage component may be pre-loaded with energy and therefore not be configured to receive energy from an external source. For example, the energy storage component can be fully charged or substantially fully charged when implanted in the patient.

In some embodiments, the system 200 includes more than one energy storage component 232. For example, the system 200 can include a first energy storage component and a second energy storage component. In some embodiments, the first energy storage component is "energy dense" and the second energy storage component is "power dense." The term "energy dense" refers to the amount of energy in a given mass or volume, while the term "power dense" refers to the amount of power in a given mass or volume. In embodiments in which the first energy storage component is energy dense, the first energy storage component can be a battery. In embodiments in which the second energy storage component is power dense, the second energy storage component can be a capacitor. Moreover, in embodiments having more than one energy storage component, one of the energy storage components (e.g., the first energy storage component) can be a primary, non-rechargeable component and another of the energy storage components (e.g., the second energy storage component) can be a secondary, rechargeable component. Furthermore, at the time when the system 200 is implanted, the first energy storage component (e.g., the battery) can be at or near its full stored energy capacity and the second energy storage component (e.g., the capacitor) can be substantially devoid of stored energy. In such embodiments, the second energy storage component can be charged after the implant procedure. In some embodiments, the second energy storage component can be charged using an energy source positioned external to the body. In other embodiments, the second energy storage component can be charged using invasive charging mechanisms, such as a catheter coupled to a power source. In such embodiments, the catheter can dock or otherwise interface with one or more implanted aspects of the system 200 to charge the second energy storage component.

In some embodiments, the energy storage component 232 can be charged (initially charged, recharged, etc.) using an energy source positioned external to the implanted device, for example a source positioned external to the patient. In some embodiments, the charging is conducted directly. In alternative embodiments, the charging is conducted by electrically connecting the energy storage component 232 to the energy receiving component 230, which captures energy from the external source, converts it to an appropriate form, and provides it to the energy storage component 232. In some embodiments the energy storage component 232 may be a secondary (rechargeable) cell (battery), such as a Lithium-Polymer or Lithium-Ion cell. In various embodiments the energy storage component 232 can be a supercapacitor (double electric-layer capacitor). In various embodiments the energy storage component 232 can be a combination of a supercapacitor and conventional capacitor, such as an aluminum electrolytic capacitor, tantalum electrolytic capacitor, or multilayer ceramic capacitor. In some embodiments, the energy receiving component 230 may receive AC magnetic or electromagnetic energy from an external energy source. The received AC energy may be converted to DC using synchronous or non-synchronous (diode) rectification. In some embodiments, the converted DC energy may be boosted and regulated to a level suitable for use by an implanted processor and other implanted electronics via a boost, buck-boost, SEPIC, Zeta, charge pump, or other switch-mode power conversion circuit. In various embodiments, the externally generated magnetic or electromagnetic field can be modulated by the energy source to encode data for transmission to the implanted electronics. In various embodiments, the load presented by the implanted electronics may be modulated to convey data to the external equipment generating the magnetic or electromagnetic field. In various embodiments, NFC (nearfield communications) techniques may be used to implement energy and/or data transfer.

In some embodiments, the energy storage component 232 can be configured to promote tissue ingrowth and/or overgrowth to become endothelialized by local tissue. For example, the energy storage component 232 can be coated with a material that promotes tissue ingrowth and/or can include various structures (e.g., lattices, mesh, and the like) that promote tissue ingrowth. In some embodiments, the energy storage component 232 includes an outer jacket material configured to promote endothelialization. In some embodiments, the energy storage component 232 can have a roughened surface (e.g., via bead blasting, knurling, chemical etching, etc.) that promotes endothelialization. Without being bound by theory, endothelization of the energy storage component 232 may reduce the thrombogenicity of the energy storage component 232 and/or may help secure the energy storage component 232 and other implanted components of the system 200 in a target position.

In some embodiments, the one or more energy storage components 232 can be coupled to or otherwise interface with the anchoring elements 220. For example, the energy storage component 232 can interface with a surface of the septal wall S, and the anchoring elements 220 can interface with the energy storage component 232 such that the anchoring element 220 do not directly engage the septal wall S.

The system 200 can also include one or more sensors (e.g., a first sensor 240a, a second sensor 240b, etc.; collectively referred to as the sensors 240). The sensors 240 can be configured to measure one or more physiologic parameters related to the system 200 or the environment proximate to the sensors 240, such as local blood pressure (e.g., LA blood pressure, RA blood pressure, etc.), flow velocity, pH, SpO2, SpC, SpMet, heart rate, cardiac output, myocardial strain, etc. The sensors can be, for example, (1) embedded in an implantable component of the system 200, (2) implanted yet spaced apart from other implantable components of the system 200, and/or (3) included on a wearable patch or device external to the body. If included on a wearable patch or device, the wearable patch or device could provide power to the sensor (e.g., RFID/NFC). In some embodiments, the wearable patch or device can also read sensor data. The sensors can be continuously recording or can be turned on at select times.

In one embodiment, the first sensor 240a is a pressure sensor positionable within the LA and the second sensor 240b is a pressure sensor positionable within the RA. In some embodiments, the system 200 can further include a processor (not shown) configured to calculate a pressure differential between the LA and the RA based on information measured by the sensors 240 or other information. As described below, the system 200 may be adjusted based on the parameters measured by the sensors 240 and/or the pressure differential or other information calculated by the processor.

In some embodiments, the sensors 240 may be configured as pressure sensors. For example, the pressure sensor can include a cavity covered by a membrane, where the membrane communicates with a strain sensing element, an element that varies the frequency of a resonant circuit, and/or other elements that vary with the deflection of the membrane and alter an electrically measurable quantity. The membrane may be in direct contact with a measurement region, conformally coated with a material directly in contact with a measurement region, and/or enclosed in a rigid vessel filled with a fluid communicating with a membrane that is in contact with a measurement region, where the fluid may be a liquid such as silicone oil or a gas such as air. Embodiments with a sensor or a conformally coated sensor directly in contact with a measurement region will additionally incorporate a means of communicating pressure information to electronics enclosed in a housing.

The system 200 also includes a flow control mechanism 250 (e.g., an actuation mechanism, a flow control assembly, an actuation assembly, etc.). The flow control mechanism 250 is configured to selectively change a geometry or other characteristic of the shunting element 202 and/or the lumen 204 to change the flow of fluid through the lumen 204. For example, the flow control mechanism 250 can be configured to selectively increase a diameter of the lumen 204 (or lumen orifice) and/or selectively decrease a diameter of the lumen 204 (or lumen orifice) in response to an input. In other embodiments, the flow control mechanism 250 is configured to otherwise affect a geometry of the lumen 204. Accordingly, the flow control mechanism 250 can be coupled to the shunting element 202 and/or can be included within the shunting element 202. For example, in some embodiments the flow control mechanism 250 is part of the shunting element 202 and at least partially defines the lumen 204. In other embodiments, the flow control mechanism 250 is spaced apart from but operably coupled to the shunting element 202.

In some embodiments, at least a portion of the flow control mechanism 250 can comprise a shape memory material. The shape memory portion can include nitinol, a nitinol-based alloy, a shape memory polymer, a pH-based shape memory material, or any other suitable material configured to move or otherwise adjust as would be understood by one of skill from the description herein. The shape memory portion can be characterized by a curve that defines the amount of deformation the portion undergoes in response to a particular input (e.g., an applied stress). For example, the flow control mechanism 250 can include a nitinol element that is configured to change shape in response to exposure to energy, such as heat. In such embodiments, the flow control mechanism 250 can be selectively actuated by applying energy directly or indirectly to the nitinol element. Additional features and examples of flow control mechanisms incorporating one or more shape memory components are described in International Patent Application No. PCT/US2020/049996, the disclosure of which is incorporated by reference herein in its entirety.

In some embodiments, the flow control mechanism 250 includes an active motor that is operably coupled to one or more actuation elements that change flow through the lumen 204. Suitable motors include electromagnetic motors, implanted battery and mechanical motors, MEMS motors, micro brushless DC motors, piezoelectric based motors, solenoids, and other motors. The flow control mechanism 250 can take other suitable forms as well. Additional features and examples of shunting devices having flow control mechanisms are described in International Patent Application No. PCT/US2020/038549, the disclosure of which is incorporated by reference herein in its entirety.

In some embodiments, the flow control mechanism 250 can be actuated using energy stored in the energy storage component 232. Accordingly, rather than directly applying energy to the flow control mechanism 250, a clinician can use a controller (described below) to actuate the flow control mechanism 250 (thereby adjusting the geometry of the shunting element 202 and/or the lumen 204) using energy stored in the energy storage component 232. This permits the clinician to decouple the process of (1) applying energy to the energy receiving component 230, and (2) adjusting the shunting element 202. Accordingly, the energy storage component 232 may store energy for a period of time (e.g., minutes, hours, days, months, etc.) and, upon a determination that the flow through the shunting element 202 should be changed, a user can direct the energy storage component 232 to release stored energy and direct it to one or more aspects of the flow control mechanism 250. In other embodiments, the system 200 can automatically direct the energy storage component 232 to release stored energy and direct it the flow control mechanism 250 to adjust a flow through the shunting element 202.

In one embodiment, the energy storage component 232 can be configured to discharge energy (e.g., in the form of a discharge pulse) to heat an actuation element of the flow control mechanism 250. For example, the energy storage component 232 may discharge energy to one or more actuation elements that are composed of a metallic material such that applying energy to the metallic material leads to resistive heating, inductive heating, or both. The metallic material can be a shape memory material such as nitinol that has been manufactured such that the resistive heating results in at least a partial transition of the material from a first material phase or state (e.g., martensitic phase, R-phase, etc.) to a second material phase or state (e.g., an R-phase, an austenitic phase, etc.). If the shape memory actuation element is deformed relative to its preferred geometry (e.g., manufactured geometry, original geometry, heat-set geometry, shape-set geometry, etc.), transitioning the shape memory actuation element from the first material phase to the second material phase can induce a geometric change in the shape memory actuation element to and/or toward its preferred geometry. The heat can therefore be applied to the one or more shape memory actuation elements to affect a property of said component (e.g., a length, width, position, stiffness, etc.). The movement of the shape memory actuation element can result in a change of the shape or dimension of the lumen 204. In some embodiments, the heated element (e.g., the shape memory actuation element) is different than the mechanism that moves to change the geometry of the shunting element 202 and/or the lumen 204. For example, the actuation element may be mechanically connected to connecting features that translate the movement of the actuation element into a change in a feature (e.g., a change in size, shape, etc.) of a different component of the device (e.g. a horizontal lumen component), as described below with reference to FIGS. 8A-8C.

In another embodiment, energy stored in energy storage components is transferred into a region of the shunting element 202 containing a material that softens or melts when heated (e.g., a wax or similar component). The softened material can enable adjustments to be made to one or more components of the device (e.g., thereby changing the shape, length, orientation, or position of the component, as described herein). Once energy is no longer being applied to this region of the shunting element 202, the material can regain its original mechanical properties (e.g., re-hardens) and any adjustments made to components are held in place.

In some embodiments, the energy storage component 232 and/or the energy receiving component 230 can be omitted and flow can be adjusted by directly applying energy to the flow control mechanism 250. In such embodiments, a portion of the flow control mechanism 250 can be configured to receive energy (e.g., heat, light, RF, ultrasound, microwave, etc.) from an energy source positioned external to the body (e.g., an RF transmitter) and, in response to the received energy, adjust the flow through the lumen 204. For example, the flow control mechanism 250 can include a heat activated shape memory element, and adjusting the lumen 204 via the flow control mechanism 250 can comprise heating the shape memory element to change the geometry of the shape memory alloy element, thereby adjusting flow through the shunting element 202, as previously described.

In some embodiments, the flow control mechanism 250 is coupled to a processor (not shown) that calculates the pressure differential between the LA and RA based, at least in part, on the measurements taken by the sensors 240. If the calculated pressure differential falls outside of a predetermined range, the processor can direct the flow control mechanism 250 to change the flow through the shunting element 202. In some embodiments, the sensors 240, the processor, and the flow control mechanism 250 operate in a closed-loop system to adjust the shunting element 202. In other embodiments, the pressure differential sensed by the sensors 240 is transmitted to a display external to the patient, and a user (e.g., a clinician) adjusts the flow through the shunting element 202 based at least in part on the measured pressure differential. In such embodiments, the physician may adjust the flow using a non-invasive energy source (e.g., an RF transmitter) and/or by interfacing with a controller 260 (described below).

As provided above, the system 200 can include a controller 260 connectable to or integrated with one or more implanted aspects of the system 200. Suitable controllers include, for example, mobile device applications, computers, dedicated controllers, etc. The controller 260 can connect to various implanted aspects of the system 200 via WiFi, Bluetooth (e.g., BLE 5.0), electromagnetic, ultrasound, radiofrequency, or other wireless means. Alternatively, the controller 260 may be coupled to implanted aspects via a wired connection. The controller 260 provides a user interface such that a user (e.g., the patient, a physician, etc.) can selectively control the system 200 via the controller. For example, a physician can input a desired flow rate, pressure/pressure gradient, or other input, and the controller 260 can communicate (either directly or indirectly) with the flow control mechanism 250 such that the flow control mechanism 250 manipulates the shunting element 202 to achieve a desired flow rate and/or flow resistance through the shunting element 202.

As discussed above, the controller 260 may be coupled to various implanted aspects of system 200 via a combination of wired and wireless connections. Distributing the communication across multiple devices and/or modalities may provide improved flexibility and power savings. It is understood that wireless communication with "deep" implants well below the skin (e.g., the implanted components of the system 200) present greater challenges with wireless data and power transmission. In some embodiments, the system 200 may utilize wireless technology to connect external components with a hub and wired technology to connect the hub to the device electronics. For example, the system 200 may communicate to a subcutaneous device via a wired connection, and the subcutaneous device communicates to an external device via a wireless connection, or vice versa.

Some embodiments of the present technology adjust the geometry of the shunting element 202 and/or the lumen 204 consistently (e.g., continuously, hourly, daily, etc.). Consistent adjustments might be made, for example, to adjust the flow of blood based on an exertion level and/or heart rate of the patient, which changes frequently over the course of a day. For example, the system 200 can have a baseline state in which the lumen 204 is substantially closed and does not allow substantial blood flow between the LA and RA, and an active state in which the lumen 204 is open and allows blood to flow between the LA and RA. The system 200 can transition from the baseline state to the active state whenever the exertion level (e.g. as measured by the heart rate) of the patient increases due to exercise, stress, or other factors. In another embodiment, consistent adjustments can be made based on, or in response to, sensed physiological parameters, including, for example, sensed LA pressure and/or RA pressure via sensors 240. If the LA pressure increases, the system 200 can automatically increase a diameter of the lumen 204 between the LA and the RA and allow increased blood flow. In another example, the system 200 can be configured to adjust based on, or in response to, an input parameter from another device such as a pulmonary arterial pressure sensor, insertable cardiac monitor, pacemaker, defibrillator, cardioverter, wearable, external ECG or PPG, and the like.

Some embodiments of the present technology adjust the geometry of the lumen 204 only after a threshold has been reached (e.g., a sufficient period of time has elapsed). This may be done, for example, to avoid unnecessary back and forth adjustments and/or avoid adjustments based on clinically insignificant changes. In some embodiments, adjustments may occur occasionally as a patient's condition changes, for example the lumen 204 may gradually open if a patient experiences a sustained rise in LA pressure (e.g., rate of change is above a predetermined threshold, or the LA pressure remains higher than a predetermined threshold for longer than a predetermined amount of time), pulmonary artery pressure, weight, or another physiologically relevant parameters. Additionally or alternatively, adjustments can occur if pressure exceeds a threshold or increases by a threshold amount over a period of time (e.g., several days or more). The geometry of the lumen 204 is then adjusted (e.g., the diameter of the lumen 204 is increased) to increase blood flow between the LA and RA and to avoid decompensation. When the patient is considered stable (e.g., if pressure or another parameter returns to normal levels), the geometry of the lumen 204 can once again be adjusted into the smaller, previous configuration.

The system 200 can also enable a clinician to periodically (e.g., monthly, bi-monthly, annually, as needed, etc.) adjust the geometry of the lumen 204 to improve patient outcomes. For example, during a patient visit, the clinician can assess a number of patient parameters and determine whether adjusting the geometry of the lumen 204, and thus altering blood flow between the LA and the RA, would provide better treatment and/or enhance the patient's quality of life. Patient parameters can include, for example, physiological parameters (e.g., LA blood pressure, RA blood pressure, the difference between LA blood pressure and RA blood pressure, flow velocity, heart rate, cardiac output, myocardial strain, etc.), subjective parameters (e.g., whether the patient is fatigued, how the patient feels during exercise, etc.), and other parameters known in the art for assessing whether a treatment for HFpEF is working. If the clinician decides to adjust the diameter of the lumen 204, the clinician can adjust the device lumen using the techniques described herein.

Figure 3:
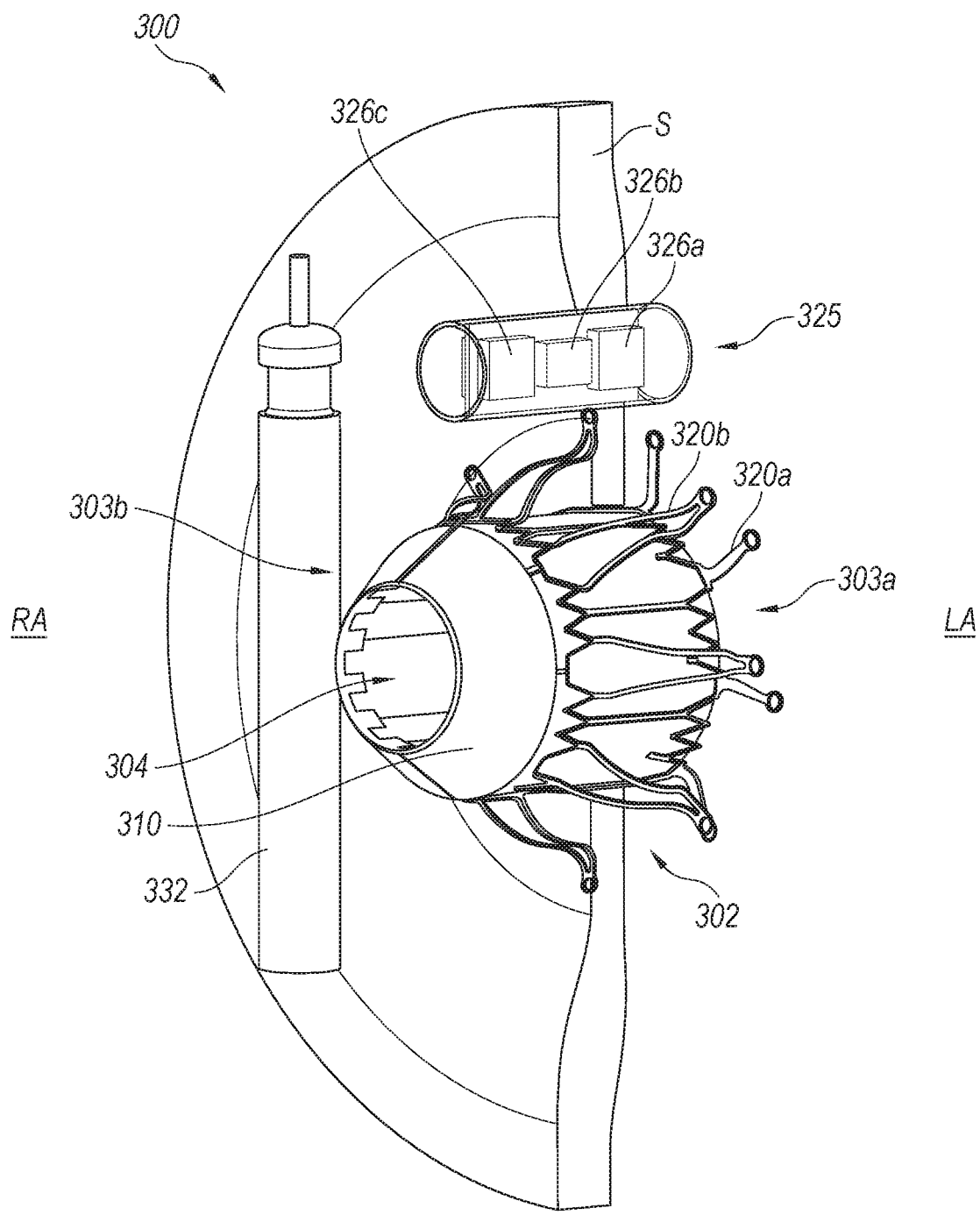
FIG. 3 is a partially cut-away isometric view of an interatrial shunting system configured in accordance with select embodiments of the present technology.

FIG. 3 is a partially cut-away isometric view of an interatrial shunting system 300 ("system 300") configured in accordance with select embodiments of the present technology. Similar to the system 200, the system 300 includes a shunting element 302 that can traverse the septal wall S such that a first end portion 303a resides within the LA and a second end portion 303b resides within the RA. The shunting element 302 can include a lumen 304 extending between the first end portion 303a and the second end portion 303b to direct fluid between the LA and the RA. The shunting element 302 can include a membrane 310 that at least partially encompasses aspects of the shunting element 302 and/or at least partially defines the lumen 304. The shunting element 302 is secured in position by first anchoring elements 320a and/or second anchoring elements 320b.

The system 300 further includes a housing 325. The housing 325 is illustrated as traversing the septal wall S, although in other embodiments the housing 325 can reside within a heart chamber (e.g., within the RA, within the LA, etc.) and/or can be positioned within or upon the septal wall S. In some embodiments, the system 300 can include multiple housings 325. In the illustrated embodiment, the housing 325 is at least partially spaced apart from the shunting element 302, although in other embodiments the housing 325 is coupled to the shunting element 302 or is integral with the shunting element 302. An outer surface of the housing 325 can comprise a biocompatible material that promotes tissue ingrowth to secure the housing 325 in place.

The housing 325 can define a fluidly isolated chamber for storing various system components, such as electrical components 326a-c (collectively referred to as electrical components 326). The electrical components 326 can include, among other things, an energy receiving component (e.g., the energy receiving component 230, shown in FIG. 2), an energy storage component (e.g., the energy storage component 232, shown in FIG. 2), a microcontroller or processor, one or more sensors (e.g., sensors 240, shown in FIG. 2), a motor, or other system component(s). In some embodiments, the housing 325 can include a first sensor (e.g., electrical component 326a) configured to be positioned within the LA for monitoring LA pressure and a second sensor (e.g., electrical component 326c) configured to be positioned within the RA for monitoring RA pressure. As discussed above, the sensors can be configured to determine a pressure differential between the LA and the RA. Without being bound by theory, having multiple sensors located within a single housing component that traverses the septal wall is useful because it enables multi-heart chamber measurements while limiting the overall size of the implanted aspects of the system 300 and reducing the complexity of the delivery procedure. Such a system also reduces the number of components and connections required to power and operate sensors that are performing measurements in multiple heart chambers, which increases the reliability of the system. In some embodiments, the system 300 further includes a separate energy storage component 332 (e.g., a battery, a supercapacitor, etc.).

The system 300 can further include a flow control mechanism (not shown), such as the flow control mechanism 250 described with respect to the system 200. The flow control mechanism can be included on and/or operably coupled to the shunting element 302 and can actively adjust a geometry of the lumen 304. In some embodiments, for example, the flow control mechanism, when actuated, manipulates one or more structural elements defining the lumen 304 and/or the shunting element 302. In some embodiments, the flow control element can include a shape memory actuator and/or a motor, as previously described. In some embodiments, one or more components of the flow control mechanism (e.g., a motor) can be positioned within the housing 325. The components positioned within the housing 325 can be coupled to the shunting element 302 (e.g., wirelessly coupled, wired, etc.) to change the shape and/or size of the lumen 304 to adjust the flow resistance therethrough.

Figure 4A:
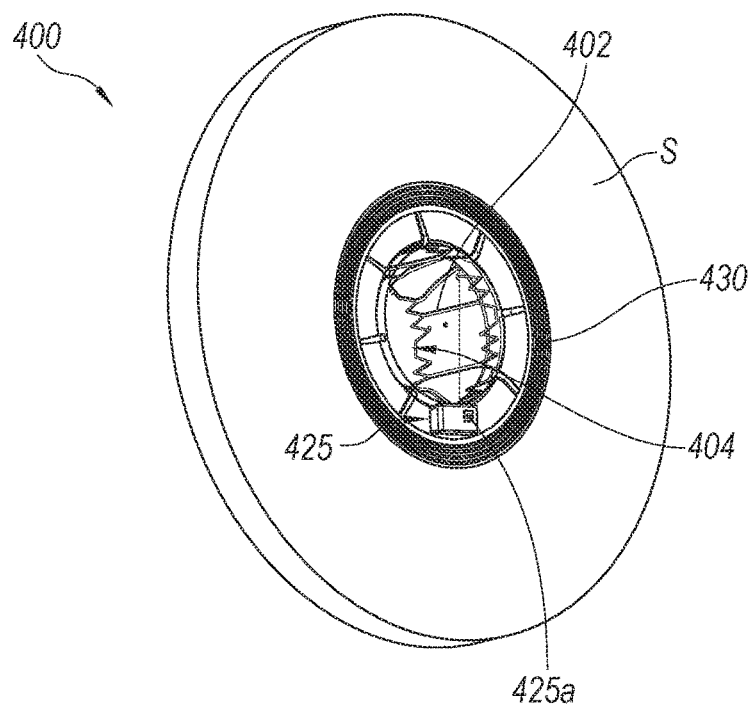
FIGS. 4A-4C illustrate an interatrial shunting system configured in accordance with select embodiments of the present technology.
Figure 4B:
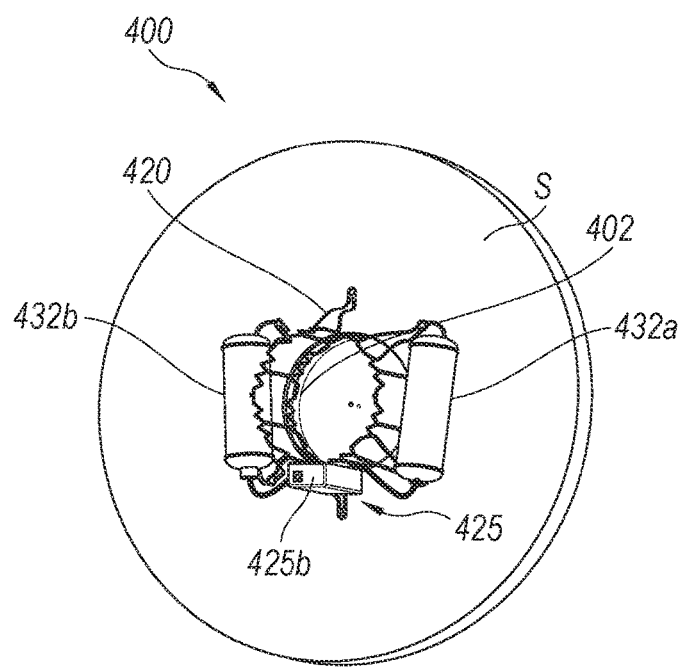
Figure 4C:
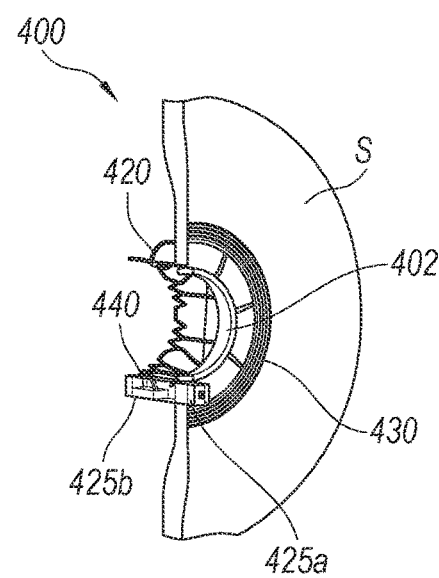

FIGS. 4A-4C illustrate an interatrial shunting system 400 ("system 400") configured in accordance with select embodiments of the present technology. More specifically, FIG. 4A is an isometric view of the system 400 from a left side of the septal wall S (e.g., viewed from the LA), FIG. 4B is an isometric view of the system 400 from a right side of the septal wall S (e.g., viewed from the RA), and FIG. 4C is a cross-sectional view of the system 400 from the left side of the septal wall S. The system 400 can have similar components to those discussed with respect to systems 200 and 300. For example, implementations of system 400 can include, among other things, a shunting element 402 having a lumen 404 extending therethrough, anchoring elements 420, a housing 425, an energy receiving component 430, a first energy storage component 432a, and a second energy storage component 432b. The shunting element 402 is positionable across the septal wall S to fluidly connect the RA and the LA. The housing 425 can also traverse the septal wall S such that a first end portion 425a resides within a first heart chamber (e.g., the LA) and a second end portion 425b resides within a second heart chamber (e.g., the RA). As discussed with respect to FIG. 3, the housing 425 can include a fluidically isolated environment for storing various electronic components, such as sensors 440 shown in FIG. 4C. The system may contain additional components, such as a microcontroller/processor and/or a controller. In some embodiments, some structures of the system may be covered with materials in order to reduce thrombogenicity, to encourage laminar flow of fluids through or around the implant, to promote endothelialization, or for other reasons. For example, in some embodiments, some structural components may be covered with a biocompatible and/or flexible material such as ePTFE, PTFE, or the like.

The one or more sensors 440 can be adapted to measure a parameter related to the device or the environment proximate to the sensor. In some embodiments, the system 400 contains one or more pressure sensors adapted to measure local pressure levels. In other embodiments, multiple pressure sensors may be included, such as the sensors 440 attached to or contained within enclosed housing 425. In some embodiments, a first pressure sensor is included in the first end portion 425a of the housing 425 to measure a pressure on a first side of the septal wall S, and a second pressure sensor is included in the second end portion 425b to measure a pressure on a second side of the septal wall S. As described above, the parameters sensed by the sensors can be used to calculate a pressure differential between two or more heart chambers. If necessary, the flow through the shunting element 402 can be adjusted based on the pressure differential. As shown in FIG. 4C, the housing 425 may span the entire length of the septal wall S such that the first end portion 425a and the second end portion 425b are each exposed to the environment in a chamber of the heart. In other embodiments, the housing 425 may traverse only a portion of the septal wall S, or may reside entirely in a single chamber of the heart. In various embodiments, the housing 425 may extend beyond the septal wall S into each of the LA and RA. In some embodiments, the system 400 can include multiple, distinct housings 425.

In various embodiments, the lumen 404 may be longer than the septal wall thickness. In various embodiments, the lumen 404 may extend beyond the face of the septal wall into one or both of the LA and RA. In various embodiments, the first sensor, second sensor, or both are positioned within the lumen 404. In various embodiments, the first sensor, second sensor, or both are positioned within an area defined by the septal defect or septal wall. In various embodiments, the first sensor, second sensor, or both are positioned outside an area defined by the septal wall and within the respective atrial chamber. In various embodiments, the housing 425 may include projections that extend off of the main housing body, for example extensions positioned to limit the amount of tissue overgrowth that will cover them. In yet other embodiments, the system 400 can include multiple, distinct housings 425.

The energy receiving component 430 can be a metallic loop or coil of multiple loops or other wire adapted to receive electromagnetic or other energy transmitted to the system 400 from an external source. In some embodiments, the loop or coil may be adapted to receive energy transmitted in the RF frequency range. In some embodiments, the energy receiving component 430 is comprised of a material such as copper or another suitable material, and can be collapsible within a delivery catheter, for example a catheter with an outer diameter no larger than 16 Fr, 18 Fr, 20 Fr, 24 Fr, 26 Fr, 27 Fr, 28 Fr, 29 Fr, 30 Fr, 35 Fr, or 40 Fr. In some embodiments, the energy receiving component 430 is configured to lie substantially flat against the septal wall S when deployed from the delivery catheter (e.g., protruding less than 2 mm into one of the chambers of the heart). In some embodiments, this may be accomplished by mechanically-coupling one or more points of the energy receiving component 430 to the anchoring elements 420, as illustrated in FIG. 4A. In the illustrated embodiment, the energy receiving component 430 is illustrated on the LA side of the septal wall S, although in other embodiments the energy receiving component may be positioned on the RA side of the septal wall S.

In some embodiments, the first energy storage component 432a and the second energy storage component 432b (collectively referred to as energy storage components 432) are positioned on an opposite side of the septal wall S relative to the energy receiving component 430. For example, in the illustrated embodiment the energy storage components 432 are positioned on a RA side of the septal wall S and the energy receiving component 430 is positioned on a LA side of the septal wall. Without being bound by theory, positioning energy capture and energy storage components on opposing sides of the septal wall can useful because it may allow for a geometry that facilitates the physics of energy transfer while allowing the overall size of the implanted components of the system 400 to remain relatively small. In other embodiments, however, the energy receiving component 430 may be positioned on the same side of the septal wall as one or more of the energy storage components 432.

Figure 5A:
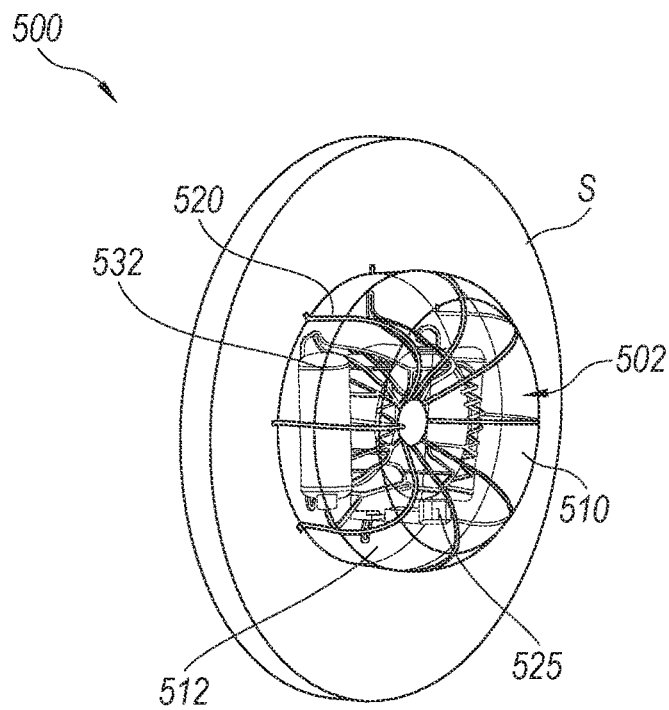
FIGS. 5A and 5B illustrate an interatrial shunting system configured in accordance with select embodiments of the present technology.
Figure 5B:
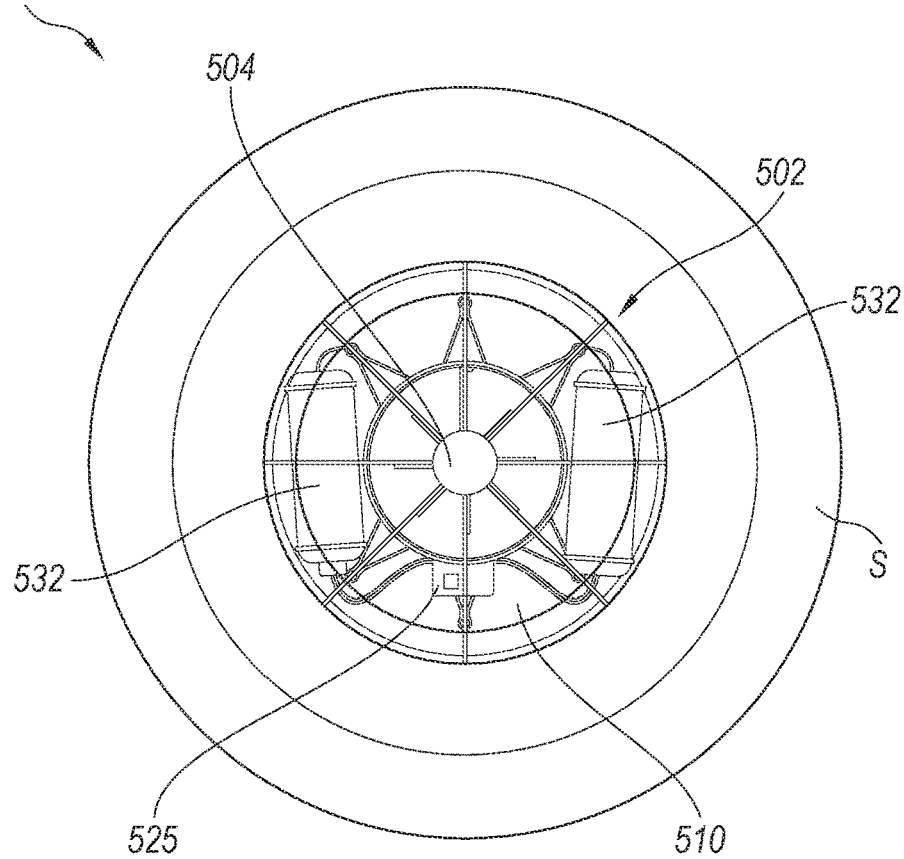

FIGS. 5A and 5B illustrate an interatrial shunting system 500 ("system 500") configured in accordance with select embodiments of the present technology. More specifically, FIG. 5A is an isometric view of the system 500 from a left side of the septal wall S (e.g., viewed from the LA), and FIG. 5B is a side view of the system 500 from the right side of the septal wall S (e.g., view from the RA). The system 500 can be generally similar to the system 400 described above with reference to FIGS. 4A-4C. Accordingly, discussion of certain features described above with respect to FIGS. 4A-4C are omitted for clarity. In addition to the features described above with respect to the system 400, the system 500 further includes a membrane 510 encasing or otherwise coupled to at least a portion of the shunting element 502. In some embodiments, the shape of the membrane 510 may be at least partially defined by structural elements 520 of the shunting element 502. In some embodiments, the structural elements 520 can further serve as anchors to secure the shunting element 502 in position and/or can define a portion of the lumen 504.

The membrane 510 can be at least partially flexible and/or impermeable, and can comprise an anti-thrombogenic, biocompatible, and/or otherwise suitable material (e.g., silicone). The membrane 510 can, among other things, provide a fluid barrier to prevent blood or other fluids from interfering with one or more components of the system 500. For example, the membrane 510 can form an enclosed chamber 512 shaped and sized to house various system components, such as the energy storage component 532. This is in contrast with the embodiment shown in FIGS. 4A-4C, in which the energy storage component 432 is directly exposed to the RA. In some embodiments, any fluid (e.g. blood) trapped under membrane 510 (e.g., within chamber 512) during deployment can be evacuated thereafter. In some embodiments, a fluid (e.g. silicon oil, a clotting agent, etc.) can be inserted into the chamber 512 after it is deployed. The fluid can provide electrical and/or thermal isolation of various system components. In some embodiments, the enclosed chamber 512 is formed between the membrane 510 and a portion of the septal wall S. In some embodiments, the housing 525 can also reside within the chamber 512, although in other embodiments the housing is positioned external to the chamber 512, such as described above with respect to FIG. 3.

The membrane 510 can also define the lumen 504 that fluidly connects the LA and the RA when the system 500 is implanted in a patient. The flexibility of the membrane 510 can enable the shunting element 502 to dynamically change in shape and or size to alter the fluid resistance through the lumen 504 while maintaining the fluidly isolated enclosed chamber 512 housing the various system components.

The systems described herein can include additional features not expressly discussed above. As a non-limiting example, the systems may include one or more components configured to transmit data and/or energy from an implanted component to a non-implanted component. For example, the systems can include a transmission element such as an antenna that can transmit data recorded by the implanted sensors to a display device external to the patient's body. The transmission element can be configured to transmit data via any suitable communication network, such as via Bluetooth, RF communication, NF communication, WiFi, cellular, or other communication protocols. In some embodiments, the systems include metallic portions (e.g., frame portions, anchor portions, etc.) that can be used for energy transmission and/or receiving purposes.

As one of skill in the art will appreciate from the disclosure herein, various components of the interatrial shunting systems described above can be omitted without deviating from the scope of the present technology. Likewise, additional components not explicitly described above may be added to the interatrial shunting systems without deviating from the scope of the present technology. Accordingly, the systems described herein are not limited to those configurations expressly identified, but rather encompasses variations and alterations of the described systems. Moreover, the following paragraphs provide additional description of various aspects of the present technology. One skilled in the art will appreciate that the following aspects can be incorporated into any of the systems described above.

C. Select Embodiments of Shunting Elements and Flow Control Mechanisms

As described above, the present technology provides interatrial shunting systems that can be selectively adjusted to control flow through the shunting element or device. Without wishing to be bound by theory, the adjustability of the shunting systems provided herein are expected to advantageously address a number of challenges associated with heart failure treatment. First, heart failure is a heterogenous disease and many patients have various co-morbidities, and the resulting disease presentation can be diverse. Accordingly, a "one size fits all" approach to heart failure treatment will not provide the same therapeutic benefit to each patient. Second, heart failure is a chronic and progress disease. Use of a non-adjustable (i.e., static) device does not permit treatment to be adapted to changes in disease progression. The adjustable shunting systems described herein, however, are expected to advantageously provide increased flexibility to better tailor treatment to a particular patient and/or to various disease stages.

Additional features of various aspects of the shunting systems, such as various embodiments of shunting devices and flow control mechanisms, are described below with respect to FIGS. 6-7C. The shunting devices described below can be adapted for use with the shunting systems described above with respect to FIGS. 2-5B. For example, any of the systems described above can incorporate some of the features described below. However, the systems described herein are not limited to the shunting devices expressly described herein. Other suitable shunting devices can be utilized, such as those described in International Patent Application Nos. PCT/US2020/049996 and PCT/US2020/038549, the disclosures of which were previously incorporated by reference herein.

Figure 6:
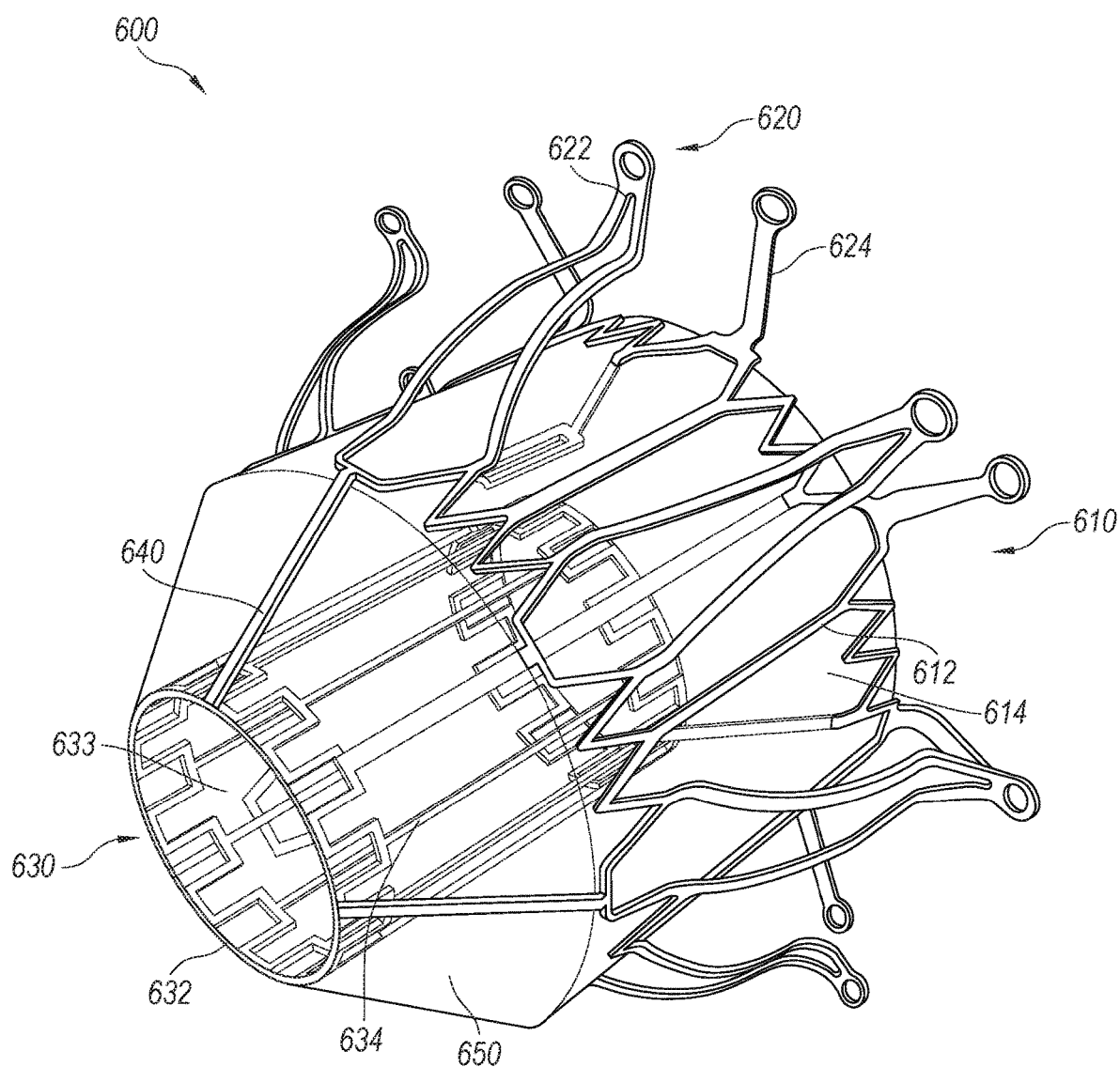
FIG. 6 illustrates an adjustable interatrial shunt device configured in accordance with select embodiments of the present technology.

FIG. 6 illustrates an exemplary adjustable interatrial shunt device 600 ("device 600") configured in accordance with embodiments of the present technology. The device 600 includes an outer frame 610 and an adjustable inner lumen 630. The frame 610 includes a plurality of arms 612 defining a scaffolding for the device 600. The frame 610 can further include a plurality of RA anchors 622 and LA anchors 624. The RA anchors 622 and the LA anchors 624 are configured to engage native heart tissue when the device 600 is implanted in a heart to secure the device 600 is place. The frame 610 can be encased in an outer membrane 614 suitable to engage native heart tissue. For example, the outer membrane 614 can be a biocompatible and/or anti-thrombogenic material or fabric, such as ePTFE, polyester, polyurethane, or silicone. In some embodiments, the outer membrane 614 is an elastomeric material that is at least partially stretchable and/or flexible. The adjustable inner lumen 630 includes a proximal end portion 632 positionable within the RA of a human heart. The adjustable inner lumen 630 may extend longitudinally along the length of the device 600, or angularly along a generally-conical plane coincident with the one or more connecting struts 640 to a distal end portion (not shown). In some embodiments, the distal end portion of the adjustable inner lumen 630 is configured to reside within the LA of the heart when the device 600 is implanted. Accordingly, in some embodiments, the adjustable inner lumen 630 can fluidly connect the LA and the RA of the heart when implanted. The adjustable inner lumen 630 is defined by a plurality of struts 634 extending along the axial length of the lumen 630 (as shown in FIG. 6) or in an angular plane generally defined by the conical shape encompassed by the connecting struts 640. In some embodiments, the plurality of struts 634 are generally parallel to a center axis of the lumen 630. The struts 634 can comprise a shape-memory material and/or a superelastic material such as nitinol, malleable materials such as stainless steel, cobalt chromium, or other suitable materials. The struts 634 can be connected to the frame 610 (e.g., the arms 612 of the frame 610) via one or more connecting struts 640. The connecting struts 640 can also comprise a shape-memory material and/or a superelastic material such as nitinol, malleable materials such as stainless steel or cobalt chromium, or other suitable materials. As described below with reference to FIGS. 7A-7C, the one or more connecting struts 640 can be actuated to alter a position of the struts 634 and change a diameter of the lumen 630 and/or lumen orifice.

The lumen 630 can further be defined by an inner membrane 633. In some embodiments, the inner membrane 633 forms a sheath around the struts 634 (e.g., the struts 634 can be embedded within the inner membrane 633). In other embodiments, the struts 634 can be positioned adjacent to but not encased within the inner membrane 633. For example, the struts 634 can be internal to the inner membrane 633 (e.g., within the lumen 630) or external to the inner membrane 633 (e.g., outside the lumen 630). When the struts 634 are not encased within the inner membrane 633, the struts 634 can be otherwise connected to the inner membrane 633, although in other embodiments the struts 634 are not connected to the inner membrane 633. Regardless of the relative positioning of the struts 634 and the inner membrane 633, the inner membrane 633 can form a single and/or continuous membrane with the outer membrane 614 of the frame 610 (in such embodiments, the outer membrane 614 and the inner membrane 633 can be collectively referred to as a single or unitary membrane). The volume of space between the outer membrane 614 and the inner membrane 633 can form a generally toroidal shaped chamber 650, as described in greater detail below. The inner membrane 633 can comprise the same material as the outer membrane 614 of the frame 610. For example, the inner membrane 633 can be a biocompatible and/or anti-thrombogenic material such as ePTFE and/or an elastomeric material that is at least partially stretchable and/or flexible. For example, in an exemplary embodiment, the inner membrane 633 is ePTFE and forms a sheath around the struts 634. In some embodiments, the inner membrane 633 and the outer membrane 614 can comprise different materials. In some embodiments, the device 600 has two, three, four, five, six, seven, eight, nine, ten, eleven, and/or twelve struts 634. As described in greater detail with respect to FIGS. 7A-7C, in some embodiments the struts 634 can be malleable and/or contain one or more hinges, enabling the struts to dynamically change shape (e.g., expand, fold, or otherwise bend), thereby changing the diameter of the inner lumen 630.

As described above, within embodiments the volume between the outer membrane 614 of the frame 610 and the inner membrane 633 of the adjustable inner lumen 630 defines a generally toroidal shaped chamber 650. The chamber 650 can be fluidly isolated from the interior of the lumen via the inner membrane 633. The chamber 650 can also be fluidly isolated from the environment surrounding the device 600 via the outer membrane 614. Accordingly, in some embodiments, the device is configured to prevent blood from flowing into the chamber 650. In some embodiments, the chamber 650 can contain a compressible and/or displaceable liquid, gas, and/or gel. Accordingly, as the diameter of the lumen is adjusted, the liquid or gas can either be compressed, expanded, and/or displaced. The chamber 650 can also house one or more electronic components (e.g., a battery, a sensor, etc.), as described above with reference to FIGS. 5A-5B. In such embodiments, the electronic components can be electrically isolated from other system components. In some embodiments, the volume between the outer membrane 614 of the frame 610 and the inner membrane 633 can be reduced or eliminated when the struts 634 are adjusted to extend only partially into the space defined by frame 610 or when the struts 634 are angled to align or nearly align with the generally-conical shaped plane defined by the connecting struts 640.

Figure 7A:
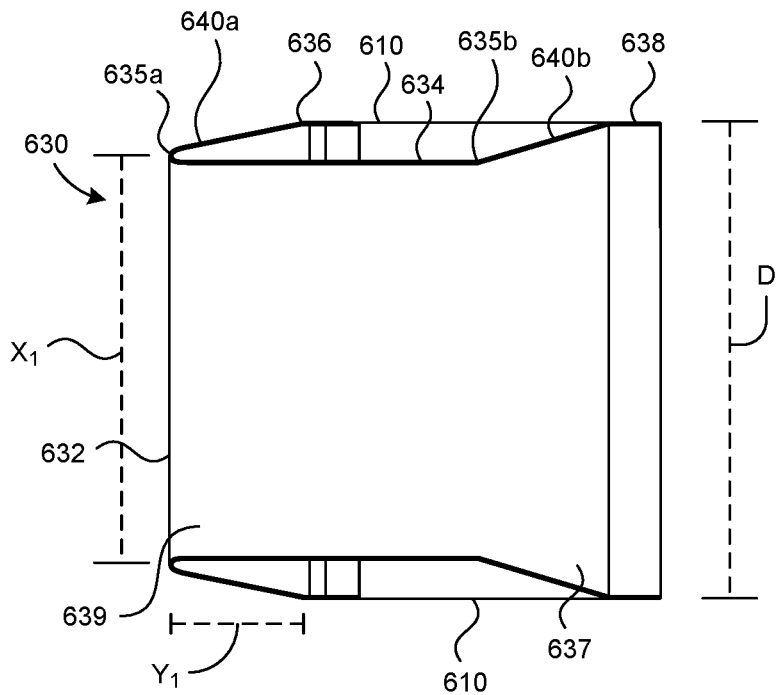
FIGS. 7A-7C are cross-sectional illustrations of the adjustable interatrial device shown in FIG. 6 and configured in accordance with select embodiments of the present technology.
Figure 7B:
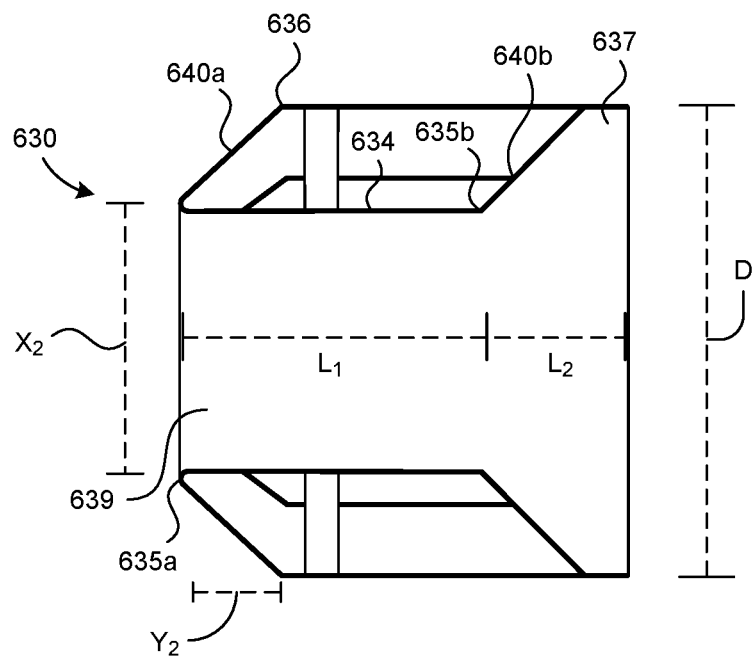
Figure 7C:
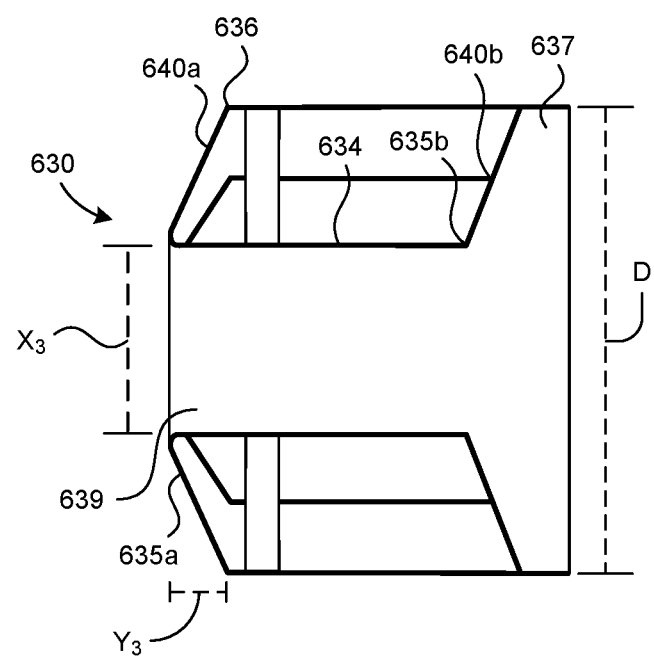

FIGS. 7A-7C schematically illustrate the adjustable inner lumen 630 of the device 600. Referring to FIG. 7A, the struts 634 are connected to the frame 610 (e.g., the arms 612, shown in FIG. 6) via a first connecting strut 640a at a proximal end (e.g., RA) portion and via a second connecting strut 640b at a position distal to the proximal end (e.g., at a location near the LA) portion (collectively referred to as "connecting struts 640"). As described above, the struts 634 at least partially define the shape of the lumen 630. The first connecting strut 640a can connect the struts 634 to the frame 610 at a proximal connection 636 on the RA side of the device 600. The second connecting strut 640b can connect the struts 634 to the frame 610 at a distal connection 638 that is distal to the RA side of the device 600 (e.g., on the extreme LA side of the device 600 as shown in FIG. 7A). The transition between the first connecting strut 640a and the strut 634 can include a hinge or other bendable aspect 635a (referred to hereinafter as "hinge 635a"). Likewise, the transition between the strut 634 and the second connecting strut 640b can also include a hinge or bendable aspect 635b (referred to hereinafter as "hinge 635b"). As will be described below, the hinges 635 enable the strut 634 to bend and/or fold relative to the first and second connecting struts 640, thereby dynamically adjusting the diameter of the inner lumen 630.

Referring to FIG. 7A, the device 600 is shown in a first configuration in which the lumen 630 defined by the struts 634 has a first inner diameter $X_1$. The frame 610 has a diameter D, and the proximal connection 636 and the hinge 635a are separated by a distance $Y_1$. To reduce the inner diameter of the lumen 630, the proximal end portion 632 of the inner lumen 630 moves distally (e.g., towards the LA), causing the struts 634 to bend at hinges 635a and 635b. More specifically, in the illustrated embodiment, the angle defined by the first connecting strut 640a and the strut 634 at hinge 635a is increased, while the angle defined by the second connecting strut 640b and the strut 634 at hinge 635b is decreased. Accordingly, in various embodiments, the struts 634 have a fixed length but are moveable through a range of positions by the connecting struts 640 to change the diameter of lumen 630. In such embodiments, the lumen 630 defined by the struts 634 remains a constant length (e.g., length $L_1$ remains substantially the same), even when the diameter of the lumen 630 is changing. Moreover, $L_1$ may be intentionally long such that the connecting struts 640a and 640b connect near the RA and LA, respectively, thereby creating a larger toroidal cavity 650. Alternatively, $L_1$ may be intentionally small such that the connecting struts 640a and 640b may be substantially proximate to one another, thereby creating a smaller or negligible toroidal cavity 650. It will be apparent to one skilled in the art that various embodiments of the present technology include the mirror of the embodiment shown in FIGS. 7A-7C, whereby the adjustable tapered diameter defining $X_1$-$X_3$ is oriented on the LA side rather than the RA side, and the fixed diameter D is oriented on the RA side rather than the LA side.

FIG. 7B illustrates a second configuration of device 600 in which the inner lumen 630 has a second inner diameter $X_2$ that is less than the first inner diameter $X_1$. The proximal connection 636 and the hinge 635a are separated by a distance $Y_2$ that is less than the distance $Y_1$. The diameter D of the frame 610 does not substantially change. FIG. 7C illustrates a third configuration of device 600 in which the inner lumen 630 has a third inner diameter $X_3$ that is less than the second inner diameter $X_2$. The proximal connection 636 and the hinge 635a are separated by a distance $Y_3$ that is less than the distance $Y_2$. The diameter D of the frame 610 does not change. As discussed above, the struts 634 and/or the connecting struts 640 can comprise a shape memory material. Accordingly, once the struts 634 and connecting struts 640 have been transitioned to a desired position, the struts can retain their configuration and the lumen retains a constant diameter until an active input is received (e.g. via an actuation mechanism, as discussed below).

In various embodiments, the device 600 is configured to adjust from a first configuration or geometry to a second configuration or geometry. In the first configuration, the lumen 630 has a first substantially constant diameter. In the second configuration, the lumen 630 has a second substantially constant diameter different than the first substantially constant diameter. The lumen may have a substantially constant diameter along all or substantially all of its entire length. In some embodiments, however, the lumen may have a substantially constant diameter along only a major portion of its length. For example, the lumen diameter may be substantially constant along the portion that extends through the septal wall. In another example, the lumen has a substantially constant diameter along its entire length, and has additional features adjacent to the lumen on one or both ends, such as a flare, funnel, taper, or the like. For example, as will be described in greater detail below, the device 600 shows the lumen 630 having a funnel shaped inflow portion 637 configured for fluid communication with a LA of a heart (not shown) and a cylindrical shaped outflow portion 639 configured for fluid communication with the right atrium of a heart (not shown).

Although FIGS. 7A-7C only illustrate three lumen diameters, one skilled in the art will appreciate that the struts 634 can be actuated through a plurality of configurations or geometries (not shown), resulting in a plurality of discrete lumen diameters (not shown). For example, the lumen 630 can take any diameter between a fully open configuration and a fully closed configuration. Moreover, in addition to decreasing the diameter of the lumen 630 as illustrated, the struts 634 can be selectively actuated via the connecting struts 640 to increase the diameter of the lumen 630. To increase the diameter of the inner lumen 630, the proximal end portion 632 of the inner lumen 630 moves proximally (e.g., further into the RA), such that the angle defined by the first connecting strut 640a and the strut 634 at hinge 635a is decreased, while the angle defined by the strut 634 and the second connecting strut 640b at hinge 635b is increased. Accordingly, device 600 enables the diameter of the lumen 630 to by selectively adjusted to control the flow of blood through the lumen 630. The specific diameter for the lumen 630 can be selected based off the patient's needs.

In some embodiments, the device 600 can be adjusted using an inflatable balloon intravascularly delivered proximate the device 600. For example, a balloon (not shown) can be delivered via a catheter and positioned within the lumen 630. Inflating the balloon can push the struts 634 radially outward, enlarging the lumen 630 (e.g., transitioning from the configuration shown in FIG. 7B to the configuration shown in FIG. 7B). The balloon can also be used to reduce the diameter of the lumen 630 by pushing the proximal end portion 632, such as at hinge 635a, distally.

In some embodiments, the device 600 can be adjusted using an actuation assembly implanted with the device (not shown). In some embodiments, the actuation assembly is included on the device and can actively adjust the inner lumen diameter by actuating one or more of the connecting struts 640, which in turn cause the struts 634 to change position. In some embodiments, for example, the actuation assembly, when actuated, pulls the proximal end portion 632 distally, causing the struts 634 to bend as described above. The actuation assembly can also be configured to directly bend the struts 634 to alter the diameter of the lumen 630. In some embodiments, the actuation assembly can be a motor. In addition, other materials that can convert energy to linear motion can be used (e.g., nitinol). In some embodiments, a nitinol element is coupled to a pall or other mechanical element moveable via actuation of the nitinol element.

The device 600 can include or be operably coupled to one or more sensors, as described above with reference to FIGS. 2-5B. The sensors can be configured to detect one or more physiological parameters, such as LA blood pressure, RA blood pressure, flow velocity, heart rate, cardiac output, myocardial strain, etc. The sensors can be, for example, (1) embedded in the device, (2) implanted yet spaced apart from the device (e.g., in the LA, RA, CS, etc.), and/or (3) included on a wearable patch or device external to the body. In some embodiments, the wearable patch or device can also read sensor data. The sensors can be continuously recording or can be turned on at select times. In one embodiment, for example, the sensors are battery powered and the battery is recharged via power harvesting. The sensors can transmit sensed physiological parameters to external display elements, external controllers, control circuitry included on the device, and/or control circuitry wirelessly coupled to the device. In some embodiments, for example, sensor data (e.g., sensed physiological parameters) can be used to actively monitor the patient and/or automatically control the adjustable devices as described herein. In another example, the sensors transmit sensor data, such as LA and/or RA pressure, to an external display element and/or a memory storage device.

In addition to the diameter of the lumen, the shape of the lumen can also promote flow through device 600. For example, referring back to FIGS. 7A-7C, the second connecting struts 640b can define a funnel shaped inflow portion 637 configured for fluid communication with a LA of a heart (not shown), and the lumen 630 can include a cylindrical shaped outflow portion 639 configured for fluid communication with the RA of the heart. As illustrated in FIG. 7B, the cylindrical shaped outflow portion 639 can have a length $L_1$ and the adjacent funnel shaped inflow portion 637 can have a length $L_2$. The diameter of the lumen 630 in the cylindrical shaped outflow portion 639 along the length $L_1$ is substantially constant. The substantially constant diameter of the lumen 630 along the length $L_1$ is less than the variable diameter of the funnel shaped inflow portion 637 along the length $L_2$. Although length $L_1$ is shown as greater than length $L_2$ in the illustrated embodiment, other embodiments have a length $L_2$ greater than length $L_1$. In some embodiments, length $L_1$ extends along a major portion of the length of the lumen 630, and length $L_2$ extends along a minor portion of the length of the lumen 630. In other embodiments, the struts 634 defining the cylindrical shaped outflow portion 639 extend between a distal inflow aperture and a proximal outflow aperture and there is no funnel shaped inflow portion 637. The cylindrical shaped outflow portion 639 can also have other non-circular cross-sectional shapes that have substantially constant inner dimensions along length $L_1$. For example, the cross-sectional shape of the outflow portion having length $L_1$ can be oval, triangular, rectangular, pentagonal, etc.

When the device 600 is implanted in a heart, blood flows into the lumen 630 at the funnel shaped inflow portion 637 (e.g., through the distal inflow aperture), through the cylindrical shaped outflow portion 639, and into the RA. In the exemplary embodiment, the combination of the funnel shaped inflow portion 637 and the cylindrical shaped outflow portion 639 are expected to provide the device 600 with a number of beneficial flow characteristics. For example, the funnel shaped inflow portion 637 can increase blood flow into the lumen 630 from the LA. The relatively larger distal inflow aperture allows for the gathering of a larger blood volume. Blood then flows from the relatively larger diameter funnel shaped inflow portion 637 to the relatively smaller diameter cylindrical shaped outflow portion 639. Based on the Venturi effect (Bernoulli's principle in mathematical terms), pressure decreases downstream and the flow velocity increases as the blood flows from the funnel shaped inflow portion 637 into the relatively smaller diameter cylindrical shaped outflow portion 639. In the exemplary embodiment, the outflow portion 639 has a cylindrical shape with a substantially constant diameter along length $L_1$. The cylindrical shaped outflow portion 639 maintains flow therethrough. By contrast, a funnel-shaped outflow would act as a diffuser. Based on Bernoulli's Principle, an increasing diameter on the outflow would decrease flow velocity. The exemplary cylindrical-shaped outflow reduces swirl effects and turbulence from the inflow while also minimizing pressure increases. Combined, these effects are expected to enhance blood flow between the LA and the RA. Additionally, as illustrated in FIGS. 7A-7C, the device retains the funnel shaped inflow portion 637 and the cylindrical shaped outflow portion 639 as it transitions between configurations.

One will appreciate from the description herein that other lumen shapes are possible and within the scope of the present technology. In some embodiments, for example, the lumen does not have the funnel shaped inlet portion but rather retains a substantially constant diameter along substantially the entire length of the lumen. For example, the lumen can be substantially cylindrical with a substantially constant diameter extending between the distal end portion and the proximal end portion. In other embodiments, the lumen is tapered and has a variable diameter extending between the distal end portion and the proximal end portion. For example, the lumen can have a relatively larger inflow aperture at the distal end portion and a relatively smaller outflow aperture at the proximal end portion, with the lumen constantly tapering inward between the inflow aperture and the outflow aperture to form a funnel shape. In yet other embodiments, the lumen can have a generally hourglass shape having a central pinch point. As discussed above, altering the shape of the lumen can affect the rate of the blood flow through the lumen. Accordingly, the shape of the lumen provides an additional mechanism for facilitating increased control over the flow of blood between the LA and the RA through shunts configured in accordance with the present technology.

Figure 8A:
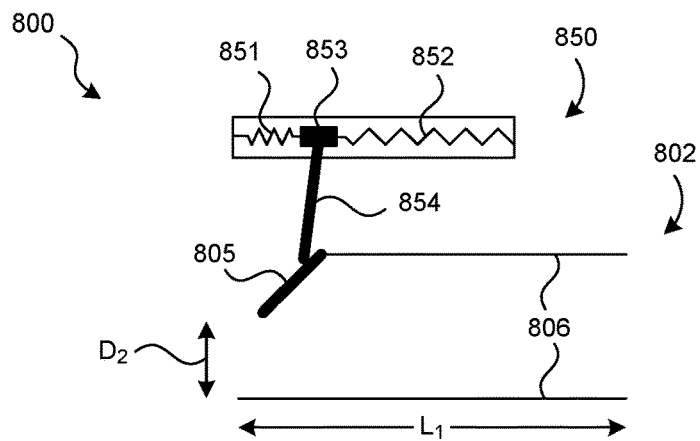
FIGS. 8A-8C illustrate various aspects of a transseptal component configured in accordance with select embodiments of the present technology.
Figure 8B:
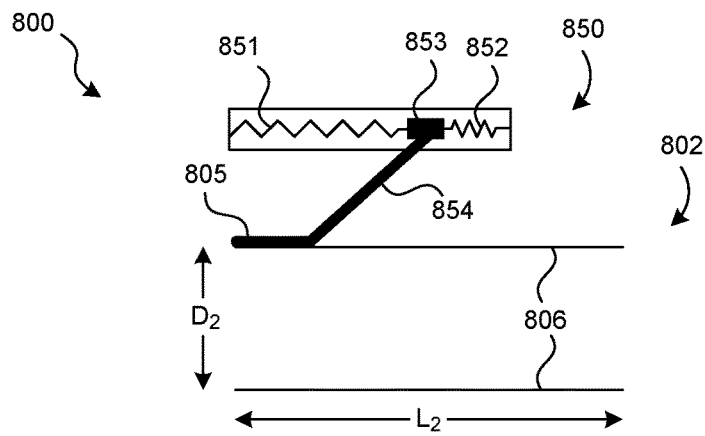
Figure 8C:
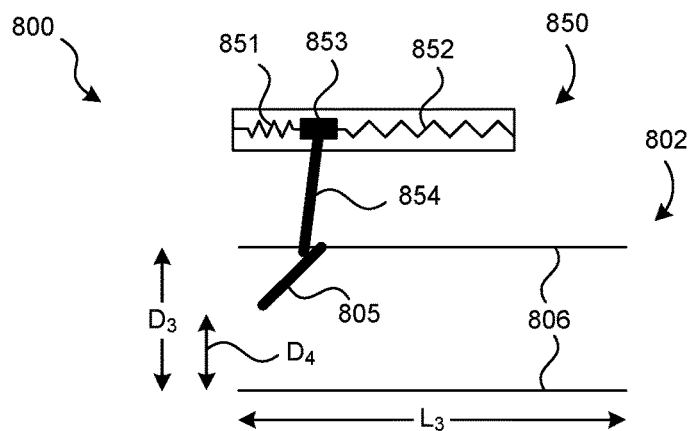

FIGS. 8A-8C illustrate another adjustable interatrial shunt device 800 ("device 800") configured in accordance with select embodiments of the present technology. In particular, FIGS. 8A-8C are cross-sectional views of the device 800, and illustrate a shunting element 802 and a flow control mechanism 850 for selectively changing a resistance to flow through the shunting element 802. Some device components and features have been removed from FIGS. 8A-8C for clarity. The flow control mechanism includes a first shape memory alloy component 851, a second shape memory alloy component 852, an actuator component 853, and a connecting strut component 854. The shunting element 802 includes an adjustable lumen strut 805 and horizontal struts 806 which may be arranged so as to create a tubular or otherwise elongated conduit through the device (i.e. from a first side of the device to a second side). FIG. 8A illustrates the device 800 in a first configuration, with first shape memory alloy component 851 in a first position which is relatively compact in length and second shape memory alloy component 852 in a first position which is relatively expanded in length. As a result, the actuator component 853 is biased in a position towards the left side of the assembly, and the connecting strut component 854 is relatively vertical. With the connecting strut component 854 in the configuration illustrated in FIG. 8A, the adjustable lumen strut 805 is angled into the tubular conduit, resulting in a relatively narrow left-side opening of the conduit created by the horizontal struts 806. This opening may be described as having a first diameter, $D_1$. In FIG. 8B, the device 800 is shown in a second configuration, which may be achieved after, for example, energy stored in an energy component (not shown) has been released to directly or indirectly heat the first shape memory alloy component 851. This heating causes the first shape memory alloy component 851 to change shape into a relatively expanded length, and the force resulting from this expansion causes the second shape memory alloy component 852 to move to a second position which is relatively compact in length. Accordingly, the actuator component 853 is driven to a second position that is more biased to the right side of the assembly, and thus the connecting strut component 854 has been moved into a second position that is relatively more horizontal in orientation and/or is more well-aligned with the horizontal struts 806 that create the fluid conduit. As a result, the left-side opening of the conduit has a relatively larger second diameter, $D_2$. In various embodiments, components of the transseptal component may be moved (either via energy application methods, mechanical adjustment methods, or other methods) that change the shape or the cross-sectional diameter of one or more sections of the conduit without changing the length of the conduit (e.g., $L_1=L_2$).

FIG. 8C is a cross-sectional view of a variation of certain aspects of the device 800 described above with respect to FIGS. 8A and 8B. Many aspects are similar to those described above in FIGS. 8A and 8B, but in this embodiment the adjustable lumen strut 805 is an internal component of the conduit defined by horizontal struts 806. The lumen diameter of devices configured as shown can be characterized by two parameters: $D_3$, which describes the diameter of the conduit defined by horizontal struts 806, and $D_4$, which describes the inner diameter of the conduit defined by the position of one or more adjustable lumen struts 805. The total length of the conduit may be described by length $L_3$. In various embodiments, movement of actuator component 853 may change the diameter $D_4$, but the sizes/lengths/diameters described by parameters $D_3$ and $L_3$ remain generally unchanged regardless of the position of the actuator component 853.

In various embodiments, a transseptal device may contain a plurality of adjustable strut arms 805, a plurality of first and second shape memory alloy components 851 and 852, a plurality of actuator components 853, and other components in various combinations. In various embodiments, energy that has been stored in an energy storage component (not shown) may not be delivered to a shape memory allow component directly (e.g. it may be delivered to an intermediate component which may then transmit energy and/or heat to the shape memory alloy component). In an example, energy stored in an energy storage component is transmitted to one or more metallic coils which interface with sections of a shape memory alloy component, and as the coils are heated resistively they transmit this heat to the shape memory alloy components.

One will appreciate from the disclosure herein that other shunting devices, shunting elements, and flow control mechanisms can be used with the shunting systems described herein. For example, in some embodiments, the shunting systems can include a gate-like valve that can move between a first position blocking or at least partially blocking a flow lumen and a second position unblocking or at least partially unblocking the flow lumen. In such embodiments, the gate-like valve can be coupled to one or more shape memory elements that can be manipulated using energy, such as energy stored in an energy storage component or energy applied directly to the shape memory element via an energy source positioned external to the patient. As another example, the shunting systems can include one or more shape memory coils wrapped around a portion of the shunting element defining the flow lumen. The shape memory coils can be selectively wound or unwound to restrict (e.g., cinch) or relax (e.g., uncinch) a portion of the flow lumen. In yet other embodiments, the shunting element can include a flexible bladder filled with a fluid or gas. The flexible bladder can be generally toroidal shaped such that it defines a flow lumen therethrough. The fluid or gas can be directed into or out of the bladder to decrease or increase the size of the lumen. In yet other embodiments, the shunting element may incorporate at least partially passive concepts that can adjust a size or shape of the flow lumen based on the pressure differential between two heart chambers. Accordingly, the systems described herein are not limited to the flow control mechanisms and/or shunting devices expressly described herein. Other suitable shunting devices can be utilized and are within the scope of the present technology, such as any of those described in International Patent Application Nos. PCT/US2020/049996 and PCT/US2020/038549, the disclosures of which were previously incorporated by reference herein

EXAMPLES

Several aspects of the present technology are set forth in the following examples:

1. A system for shunting blood between a left atrium and a right atrium of a patient, the system comprising:
   a shunting element having a lumen extending therethrough between a first orifice positionable in the left atrium and a second orifice positionable in the right atrium, wherein the lumen is configured to fluidly couple the left atrium and the right atrium when the shunting element is implanted in the patient;
   an implantable energy receiving component configured to receive energy; and
   an implantable energy storage component configured to be in electrical communication with the energy receiving component,
   wherein the energy stored within the energy storage component can be used to selectively adjust a geometry of the lumen, the first orifice, and/or the second orifice.

2. The system of example 1, further comprising an actuation mechanism configured to selectively adjust the geometry of the lumen, the first orifice, and/or the second orifice, wherein
   the energy receiving component is configured to receive energy from an energy source positioned external to the patient; and
   the energy storage component is further configured to (a) store energy received by the energy receiving component and (b) selectively release the stored energy to power the actuation mechanism.

3. The system of example 2 wherein the actuation mechanism comprises one or more shape memory elements, and wherein the energy storage component is configured to release the stored energy to heat the one or more shape memory elements.

4. The system of example 2 or 3 wherein the energy receiving component is a metallic wire configured to (i) receive energy from the energy source positioned external to the patient, and/or (ii) generate energy when exposed to a magnetic or electric field generated by the energy source positioned external to the patient.

5. The system of example 1 wherein the energy receiving component is configured to receive energy released from the energy storage component, and wherein the energy received at the energy receiving component is used to selectively adjust the geometry of the lumen, the first orifice, and/or the second orifice.

6. The system of example 5 wherein the energy receiving component includes a shape memory actuation element configured to selectively adjust the geometry of the lumen, the first orifice, and/or the second orifice.

7. The system of example 6 wherein the energy received at the energy receiving component heats the shape memory actuation element to selectively adjust the geometry of the lumen, the first orifice, and/or the second orifice.

8. A system for shunting blood between a left atrium and a right atrium of a patient, the system comprising:
   a shunting element having a lumen extending therethrough between a first orifice positionable in the left atrium and a second orifice positionable in the right atrium, wherein the lumen is configured to fluidly couple the left atrium and the right atrium when the shunting element is implanted in the patient;
   an actuation mechanism configured to selectively adjust a geometry of the lumen, the first orifice, and/or the second orifice;

an implantable energy receiving component configured to receive energy from an energy source; and an implantable energy storage component configured to store energy received by the implantable energy receiving component, wherein the implantable energy storage component is further configured to selectively release the stored energy to power the actuation mechanism and/or one or more active components of the system.

9. The system of example 8 wherein, when implanted, the energy receiving component and the energy storage components are configured to reside on opposite sides of a septal wall of the patient.

10. The system of example 8 or 9 wherein the energy storage component includes one or more tissue ingrowth features configured to promote endothelialization of the energy storage component.

11. The system of example 10 wherein the one or more tissue ingrowth features includes an external coating, a lattice structure, a roughened surface, and/or a mesh structure.

12. The system of any of examples 8-11 wherein the energy storage component includes a battery or a capacitor.

13. The system of any of examples 8-12 wherein the energy storage component is a first energy storage component, the system further comprising a second energy storage component.

14. The system of example 13 wherein the first energy storage component includes a battery and the second energy storage component includes a supercapacitor.

15. The system of any of examples 8-14 wherein the energy receiving component includes a metallic wire configured to (i) receive energy from the energy source, and/or (ii) generate energy when exposed to a magnetic or electric field generated by the energy source.

16. The system of any of examples 8-15 wherein the energy receiving component is configured to receive energy from an energy source positioned external to the patient.

17. The system of any of examples 8-16 wherein the energy storage component is configured to selectively release the stored energy to actuate the actuation mechanism.

18. The system of example 17 wherein the actuation mechanism comprises one or more shape memory elements, and wherein the energy storage component is configured to release the stored energy to heat the one or more shape memory elements.

19. The system of example 18 wherein the shape memory elements have a transition temperature, and wherein the energy storage component is configured to release sufficient energy to heat the one or more shape memory elements to a temperature above the transition temperature.

20. The system of any of examples 8-19 wherein the shunting element has an outer diameter and the lumen has lumen diameter, and wherein the actuation mechanism is configured to selectively adjust the lumen diameter without substantially changing the outer diameter.

21. The system of any of examples 8-20 wherein the actuation mechanism includes a motor, and wherein the energy storage component is configured to selectively release stored energy to power the motor.

22. The system of any of examples 8-21 wherein the one or more active components include one or more sensors configured to measure one or more physiologic parameters in the patient, and wherein the energy storage element is configured to selectively release stored energy to power the one or more sensors.

23. The system of example 22 wherein the one or more sensors include a first sensor implantable within the patient to measure a first physiologic parameter in the left atrium and a second sensor implantable into the patient to measure a second physiologic parameter in the right atrium.

24. The system of example 23, further comprising an implantable housing configured to traverse the septal wall, wherein the housing comprises:

a first end portion configured to extend into the left atrium, wherein the first end portion houses the first sensor; and a second end portion configured to extend into the right atrium, wherein the second end portion houses the second sensor.

25. The system of example 23 or 24 wherein the first physiologic parameter is a left atrial pressure and the second physiologic parameter is a right atrial pressure.

26. The system of example 25, further comprising a processor configured to calculate a pressure differential between the left atrium and the right atrium based, at least in part, on the measured first physiologic parameter and the measured second physiologic parameter.

27. The system of example 26, further comprising a controller configured to direct the actuation mechanism to selectively adjust the geometry of the lumen, the first orifice, and/or the second orifice based at least in part on the first and/or second physiologic parameter and/or the pressure differential between the left atrium and the right atrium.

28. The system of example 27 wherein the controller is configured to adjust the actuation mechanism if the pressure differential exceeds a predetermined upper threshold and/or falls below a predetermined lower threshold.

29. The system of example 27 wherein the controller is configured to adjust the actuation mechanism if a rate of change in the pressure differential exceeds a predetermined threshold.

30. The system of any of examples 8-29, further comprising a controller, wherein the controller is wirelessly connected to at least one of the shunting element, the actuation mechanism, the energy receiving component, or the energy storage component, and wherein the controller provides a user interface for initiating actuation of the actuation mechanism.

31. The system of any of examples 8-30, further comprising an implantable housing, wherein the housing includes a chamber configured for fluid isolation from the environment external to the housing, and wherein the chamber includes one or more components of the system.

32. The system of example 31 wherein the housing has a first end portion configured to be positioned within the left atrium and a second end portion configured to be positioned within the right atrium.

33. The system of any of examples 8-32, further comprising a membrane coupled to the shunting element, and wherein:

the membrane defines a chamber with the septal wall when the shunting element is implanted in the patient;

the chamber is fluidly isolated from the left atrium and the right atrium; and the energy receiving component, the energy storage component, the actuation mechanism, and/or the housing are positioned within the chamber.

34. A system for shunting blood between a left atrium and a right atrium of a patient, the system comprising:

a shunting element implantable across a septal wall of the patient such that, when implanted in the patient, the shunting element is configured to fluidly connect the left atrium and the right atrium of the patient;

an implantable energy receiving component configured to be positioned on a first side of the septal wall, the energy receiving component further configured to receive energy; and an implantable energy storage component configured to be positioned on a second side of the septal wall opposite the first side, the energy storage component further configured to (i) store energy received by the implantable energy receiving component, and/or (ii) selectively release stored energy to power one or more active components of the system.

35. The system of example 34 wherein the energy storage component is configured to store energy received by the implantable energy receiving component.

36. The system of example 34 wherein the energy storage component is configured to selectively release stored energy to power the one or more active components of the system.

37. The system of example 34 wherein the energy storage component is configured to (i) store energy received by the implanted energy receiving component, and (ii) selectively release the stored energy to power the one or more active components of the system.

38. The system of any of examples 34-37 wherein the first side of the septal wall is a left atrial side, and wherein the second side of the septal wall is the right atrial side.

39. The system of any of examples 34-38 wherein the first side of the septal wall is a right atrial side, and wherein the second side of the septal wall is a left atrial side.

40. The system of any of examples 34-39 wherein the one or more active components of the system includes one or more sensors configured to measure a physiologic parameter of the patient.

41. The system of example 40 wherein the one or more sensors are configured to measure blood pressure, flow velocity, pH, SpO2, SpC, SpMet, heart rate, cardiac output, and/or myocardial strain.

42. The system of any of examples 34-41 wherein the one or more active components includes an actuation mechanism configured to selectively adjust a geometry of the shunting element.

43. The system of example 34 wherein the one or more active components includes the energy receiving component, and wherein the energy receiving component is configured to receive energy from the energy storage component.

44. The system of example 43 wherein the energy receiving component includes an actuation element configured to selectively adjust a geometry of the shunting element.

45. The system of any of examples 34-44 wherein the energy receiving component is configured to receive energy from an energy source positioned external to the patient.

46. A method for selectively controlling blood flow between a left atrium and a right atrium in a patient using an adjustable interatrial shunting system having a lumen fluidly connecting the left atrium and the right atrium, the method comprising:

receiving, via an implanted energy receiving component, energy from an energy source positioned external to the patient;

transferring the energy received at the implanted energy receiving component to an implanted energy storage component, wherein the energy storage component stores the energy; and selectively releasing the stored energy from the implanted energy storage component to adjust a geometry of the lumen and selectively alter a flow therethrough.

47. The method of example 46 wherein receiving the energy comprises receiving radiofrequency and/or magnetic energy.

48. The method of example 46 or 47, further comprising measuring, via one or more sensors, one or more physiologic parameters.

49. The method of example 48, further comprising determining, based at least in part on the one or more measured physiologic parameters, a pressure differential between the left atrium and the right atrium.

50. The method of example 49 wherein adjusting the diameter of the lumen is based at least in part on the determined pressure differential falling outside of a predetermined range.

51. A system for shunting blood between a left atrium and a right atrium of a patient, the system comprising:

a shunting element having a lumen extending therethrough, wherein the lumen is configured to fluidly couple the left atrium and the right atrium when the shunting element is implanted in the patient;

an energy receiving component configured to receive energy from an energy source positioned external to the patient; and an actuation mechanism configured to selectively alter a size and/or shape of the lumen via energy received by the energy receiving component.

52. The system of example 51, further comprising an energy storage component, wherein the energy storage component is configured to store energy received by the energy receiving component.

53. The system of example 52 wherein the energy stored in the energy storage component can be used to actuate the actuation mechanism.

54. The system of any of examples 51-53 wherein the shunting element has an outer diameter and the lumen has lumen diameter, and wherein the actuation mechanism is configured to selectively alter the lumen diameter without substantially changing the outer diameter.

55. The system of any of examples 51-54 wherein the shunting element comprises one or more shape memory elements at least partially defining the lumen, and wherein the actuation mechanism is configured to apply energy to the one or more shape memory elements to change the size and/or shape of the lumen.

56. The system of example 55 wherein the shape memory elements have a transition temperature, and wherein the actuation mechanism is configured to heat the one or more shape memory elements to a temperature above the transition temperature.

57. The system of example 55 or 56 wherein the energy causes a strain in the shape memory elements along a stress-strain curve of the shape memory elements.

58. The system of any of examples 51-57 wherein the actuation mechanism comprises one or more shape memory elements, and wherein the one or more shape memory elements are configured to change shape to selectively alter the size and/or shape of the lumen.

59. The system of any of examples 51-58 wherein the actuation mechanism includes a motor.

60. The system of any of examples 51-59, further comprising a first sensor implantable within the patient to measure a first physiologic parameter in the left atrium and a second sensor implantable into the patient to measure a second physiologic parameter in the right atrium.

61. The system of example 60 wherein the first physiologic parameter is a left atrial pressure and the second physiologic parameter is a right atrial pressure.

62. The system of examples 60 or 61, further comprising a processor configured to calculate a pressure differential between the left atrium and the right atrium based at least in part on the measured first physiologic parameter and the measured second physiologic parameter.

63. The system of any of examples 60-62 further comprising a controller configured to direct the actuation mechanism to selectively alter a size and/or shape of the lumen based at least in part on the first and/or second physiologic parameter and/or the pressure differential between the left atrium and the right atrium.

64. The system of example 63 wherein the controller is configured to adjust the actuation mechanism if the pressure differential exceeds a predetermined upper threshold and/or falls below a predetermined lower threshold.

65. The system of example 63 wherein the controller is configured to adjust the actuation mechanism is a rate of change in the pressure differential exceeds a predetermined threshold.

66. The system of any of examples 51-65, further comprising a controller, wherein the controller is wirelessly connected to at least one of the shunting element, the actuation mechanism, or the energy receiving component, and wherein the controller provides a user interface for initiating actuation of the actuation mechanism.

67. The system of any of examples 51-66, further comprising an implantable housing, wherein the housing includes a chamber configured for fluid isolation from the environment external to the housing.

68. The system of example 67 wherein the housing has a first end portion configured to be positioned within the left atrium and a second end portion configured to be positioned within the right atrium.

69. The system of example 68 wherein the first sensor is positioned adjacent the first end portion of the housing and the second sensor is positioned adjacent the second end portion of the housing.

70. The system of any of examples 51-69, further comprising a membrane coupled to the shunting element, wherein, when the shunting element is implanted in the patient, the membrane defines a chamber with the septal wall, and wherein the energy receiving component, the energy storage component, the actuation mechanism, and/or the housing are positioned within the chamber.

71. A method for selectively controlling flow between a left atrium and a right atrium in a patient using an adjustable interatrial shunting system having a lumen fluidly connecting the left atrium and the right atrium, the method comprising:
receiving energy from an energy source positioned external to the patient; and
adjusting a diameter of the lumen using the energy, wherein adjusting the diameter of the lumen alters a flow through the lumen.

72. The method of example 71, further comprising storing the energy in an energy storage component after receiving the energy and before adjusting the diameter of the lumen using the energy.

73. The method of example 70 or 71 wherein receiving the energy comprises receiving radiofrequency and/or magnetic energy.

74. The method of any of examples 71-73, further comprising measuring, via one or more sensors, one or more physiologic parameters.

75. The method of example 74, further comprising determining, based at least in part on the one or more measured physiologic parameters, a pressure differential between the left atrium and the right atrium.

76. The method of example 75 wherein adjusting the diameter of the lumen is based at least in part on the determined pressure differential falling outside of a predetermined range.

77. A method for selectively controlling flow between a left atrium and a right atrium in a patient using an adjustable interatrial shunting system having a lumen fluidly connecting the left atrium and the right atrium, the method comprising:
receiving a signal from a signal-source positioned external to the patient; and
in response to the signal, adjusting a diameter of the lumen to alter the flow therethrough.

78. The method of example 77 wherein adjusting a diameter of the lumen comprises applying heat to one or more elements operably coupled to or defining the lumen.

79. A septal implant, comprising:
a lumen configured to fluidly connect a first side of the septal wall with a second side of the septal wall when the septal implant is implanted in a heart; and
one or more energy storage components, wherein the one or more energy storage components are configured to become endothelialized by local tissues.

80. The septal implant of example 79 wherein the one or more energy storage components include an external coating configured to promote endothelialization.

81. The septal implant of example 79 or 80 wherein the one or more energy storage components include an outer jacket material configured to promote endothelialization.

82. The septal implant of any of examples 79-81 wherein the energy storage components are configured to (i) store energy delivered from a source external to the body, and (ii) deliver the stored energy to a portion of the septal implant to change a shape or other characteristic of the lumen.

83. A septal implant, comprising:
an elongated tubular element configured to traverse the septal wall and fluidly connect a first side of the septal wall with a second side of the septal wall when implanted in a heart;
a first electronic component positioned on the first side of the septal wall when the septal implant is implanted in the heart; and
a second electronic component positioned on the second side of the septal wall when the septal implant is implanted in the heart.

84. The septal implant of example 83 wherein the first electronic component is an energy receiving element and the second electronic component is an energy storage element.

85. The septal implant of example 83 or 84 wherein the first electronic extends less than 6*mm* away from the septal wall.

86. The septal implant of any of examples 83-85, further comprising anchoring elements configured to secure the elongated tubular element in a desired position, wherein the first electronic component and/or the second electronic component are disposed between the anchoring elements and the septal wall.

87. The septal implant of any of examples 83-86, further comprising a membrane encasing at least a portion of the septal implant and configured to define one or more chambers fluidly isolated form blood within the heart.

88. The septal implant of example 87 wherein the first electronic component and/or the second electronic component are positioned within the one or more chambers.

89. The septal implant of example 87 wherein the one or more chambers are configured to be at least partially filled with a fluid after the septal implant is implanted.

90. A method for adjusting a shape of a septal implant implanted in a patient, the method comprising:
   directing energy to an energy receiving component coupled with the septal implant, wherein the energy is directed from an energy source positioned external to the patient and stored in the energy storage component; and
   selectively adjusting the shape of the septal implant by releasing stored energy from the energy storage component.

91. The method of example 90 wherein selectively adjusting the shape of the septal implant comprises selectively heating one or more components of the septal implant using the released energy.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the left atrium and right atrium, the left ventricle and the right ventricle, or the left atrium and the coronary sinus, it should be appreciated that similar embodiments could be utilized for shunts between other chambers of heart or for shunts in other regions of the body.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for shunting blood between a left atrium and a right atrium of a patient, the system comprising:
   a shunting element having a lumen extending therethrough between a first orifice positionable in the left atrium and a second orifice positionable in the right atrium, wherein the lumen is configured to fluidly couple the left atrium and the right atrium when the shunting element is implanted in the patient;
   an implantable energy receiving component configured to receive energy; and
   an implantable energy storage component configured to be in electrical communication with the energy receiving component,
   wherein the energy stored within the energy storage component can be used to selectively adjust a geometry of the lumen, the first orifice, and/or the second orifice.

2. The system of claim 1, further comprising an actuation mechanism configured to selectively adjust the geometry of the lumen, the first orifice, and/or the second orifice, wherein
the energy receiving component is configured to receive energy from an energy source positioned external to the patient; and
the energy storage component is further configured to (a) store energy received by the energy receiving component and (b) selectively release the stored energy to power the actuation mechanism.

3. The system of claim 2 wherein the actuation mechanism comprises one or more shape memory elements, and wherein the energy storage component is configured to release the stored energy to heat the one or more shape memory elements.

4. The system of claim 2 wherein the energy receiving component is a metallic wire configured to (i) receive energy from the energy source positioned external to the patient, and/or (ii) generate energy when exposed to a magnetic or electric field generated by the energy source positioned external to the patient.

5. The system of claim 1 wherein the energy receiving component is configured to receive energy released from the energy storage component, and wherein the energy received at the energy receiving component is used to selectively adjust the geometry of the lumen, the first orifice, and/or the second orifice.

6. The system of claim 5 wherein the energy receiving component includes a shape memory actuation element configured to selectively adjust the geometry of the lumen, the first orifice, and/or the second orifice.

7. The system of claim 6 wherein the energy received at the energy receiving component heats the shape memory actuation element to selectively adjust the geometry of the lumen, the first orifice, and/or the second orifice.

8. A system for shunting blood between a left atrium and a right atrium of a patient, the system comprising:
a shunting element having a lumen extending therethrough between a first orifice positionable in the left atrium and a second orifice positionable in the right atrium, wherein the lumen is configured to fluidly couple the left atrium and the right atrium when the shunting element is implanted in the patient;
an actuation mechanism configured to selectively adjust a geometry of the lumen, the first orifice, and/or the second orifice;
an implantable energy receiving component configured to receive energy from an energy source; and
an implantable energy storage component configured to store energy received by the implantable energy receiving component, wherein the implantable energy storage component is further configured to selectively release the stored energy to power the actuation mechanism and/or one or more active components of the system.

9. The system of claim 8 wherein, when implanted, the energy receiving component and the energy storage components are configured to reside on opposite sides of a septal wall of the patient.

10. The system of claim 8 wherein the energy storage component includes one or more tissue ingrowth features configured to promote endothelialization of the energy storage component.

11. The system of claim 10 wherein the one or more tissue ingrowth features includes an external coating, a lattice structure, a roughened surface, and/or a mesh structure.

12. The system of claim 8 wherein the energy storage component includes a battery or a capacitor.

13. The system of claim 8 wherein the energy storage component is a first energy storage component, the system further comprising a second energy storage component.

14. The system of claim 13 wherein the first energy storage component includes a battery and the second energy storage component includes a supercapacitor.

15. The system of claim 8 wherein the energy receiving component includes a metallic wire configured to (i) receive energy from the energy source, and/or (ii) generate energy when exposed to a magnetic or electric field generated by the energy source.

16. The system of claim 8 wherein the energy receiving component is configured to receive energy from an energy source positioned external to the patient.

17. The system of claim 8 wherein the energy storage component is configured to selectively release the stored energy to actuate the actuation mechanism.

18. The system of any of claim 17 wherein the actuation mechanism comprises one or more shape memory elements, and wherein the energy storage component is configured to release the stored energy to heat the one or more shape memory elements.

19. The system of claim 18 wherein the shape memory elements have a transition temperature, and wherein the energy storage component is configured to release sufficient energy to heat the one or more shape memory elements to a temperature above the transition temperature.

20. The system of claim 8 wherein the shunting element has an outer diameter and the lumen has lumen diameter, and wherein the actuation mechanism is configured to selectively adjust the lumen diameter without substantially changing the outer diameter.

21. The system of claim 8 wherein the actuation mechanism includes a motor, and wherein the energy storage component is configured to selectively release stored energy to power the motor.

22. The system of claim 8 wherein the one or more active components include one or more sensors configured to measure one or more physiologic parameters in the patient, and wherein the energy storage component is configured to selectively release stored energy to power the one or more sensors.

23. The system of claim 22 wherein the one or more sensors include a first sensor implantable within the patient to measure a first physiologic parameter in the left atrium and a second sensor implantable into the patient to measure a second physiologic parameter in the right atrium.

24. The system of claim 23, further comprising an implantable housing configured to traverse the septal wall, wherein the housing comprises:
a first end portion configured to extend into the left atrium, wherein the first end portion houses the first sensor; and
a second end portion configured to extend into the right atrium, wherein the second end portion houses the second sensor.

25. The system of claim 23 wherein the first physiologic parameter is a left atrial pressure and the second physiologic parameter is a right atrial pressure.

26. The system of claim 25, further comprising a processor configured to calculate a pressure differential between the left atrium and the right atrium based, at least in part, on the measured first physiologic parameter and the measured second physiologic parameter.

27. The system of claim 26, further comprising a controller configured to direct the actuation mechanism to selectively adjust the geometry of the lumen, the first orifice, and/or the second orifice based at least in part on the first and/or second physiologic parameter and/or the pressure differential between the left atrium and the right atrium.

28. The system of claim 27 wherein the controller is configured to adjust the actuation mechanism if the pressure differential exceeds a predetermined upper threshold and/or falls below a predetermined lower threshold.

29. The system of claim 27 wherein the controller is configured to adjust the actuation mechanism if a rate of change in the pressure differential exceeds a predetermined threshold.

30. The system of claim 8, further comprising a controller, wherein the controller is wirelessly connected to at least one of the shunting element, the actuation mechanism, the energy receiving component, or the energy storage component, and wherein the controller provides a user interface for initiating actuation of the actuation mechanism.

31. The system of claim 8, further comprising an implantable housing, wherein the housing includes a chamber configured for fluid isolation from the environment external to the housing, and wherein the chamber includes one or more components of the system.

32. The system of claim 31 wherein the housing has a first end portion configured to be positioned within the left atrium and a second end portion configured to be positioned within the right atrium.

33. The system of claim 8, further comprising a membrane coupled to the shunting element, and wherein:
the membrane defines a chamber with the septal wall when the shunting element is implanted in the patient;
the chamber is fluidly isolated from the left atrium and the right atrium; and
the energy receiving component, the energy storage component, the actuation mechanism, and/or the housing are positioned within the chamber.

34. A system for shunting blood between a left atrium and a right atrium of a patient, the system comprising:
a shunting element implantable across a septal wall of the patient such that, when implanted in the patient, the shunting element is configured to fluidly connect the left atrium and the right atrium of the patient;
an implantable energy receiving component configured to be positioned on a first side of the septal wall, the energy receiving component further configured to receive energy; and
an implantable energy storage component configured to be positioned on a second side of the septal wall opposite the first side, the energy storage component further configured to (i) store energy received by the implantable energy receiving component, and/or (ii) selectively release stored energy to power one or more active components of the system, wherein the energy receiving component includes an actuation element configured to selectively adjust a geometry of the shunting element.

35. The system of claim 34 wherein the energy storage component is configured to store energy received by the implantable energy receiving component.

36. The system of claim 34 wherein the energy storage component is configured to selectively release stored energy to power the one or more active components of the system.

37. The system of claim 34 wherein the energy storage component is configured to (i) store energy received by the implanted energy receiving component, and (ii) selectively release the stored energy to power the one or more active components of the system.

38. The system of claim 34 wherein the first side of the septal wall is a left atrial side, and wherein the second side of the septal wall is the right atrial side.

39. The system of claim 34 wherein the first side of the septal wall is a right atrial side, and wherein the second side of the septal wall is a left atrial side.

40. The system of claim 34 wherein the one or more active components of the system includes one or more sensors configured to measure a physiologic parameter of the patient.

41. The system of claim 40 wherein the one or more sensors are configured to measure blood pressure, flow velocity, pH, SpO2, SpC, SpMet, heart rate, cardiac output, and/or myocardial strain.

42. The system of claim 34 wherein the one or more active components includes an actuation mechanism configured to selectively adjust a geometry of the shunting element.

43. The system of claim 34 wherein the one or more active components includes the energy receiving component, and wherein the energy receiving component is configured to receive energy from the energy storage component.

44. The system of claim 34 wherein the energy receiving component is configured to receive energy from an energy source positioned external to the patient.

* * * * *